United States Patent
Revie et al.

(10) Patent No.: US 10,582,896 B2
(45) Date of Patent: Mar. 10, 2020

(54) ORTHOPAEDIC MONITORING SYSTEM, METHODS AND APPARATUS

(71) Applicant: DePuy International Limited, Leeds (GB)

(72) Inventors: Ian Revie, Boroughbridge (GB); Alan Ashby, York (GB); Dudi Reznick, Shimshit (IL); Yaacov Nitzan, Hertzelia (IL)

(73) Assignee: DePuy International Limited, Leeds, West Yorkshire (GB)

( * ) Notice: Subject to any disclaimer, the term of this patent is extended or adjusted under 35 U.S.C. 154(b) by 596 days.

(21) Appl. No.: 14/753,351

(22) Filed: Jun. 29, 2015

(65) Prior Publication Data

US 2015/0313546 A1 Nov. 5, 2015

Related U.S. Application Data

(63) Continuation of application No. 10/598,600, filed as application No. PCT/GB2005/000854 on Mar. 7, 2005, now Pat. No. 9,380,980.

(Continued)

(30) Foreign Application Priority Data

Mar. 5, 2004 (GB) .................................. 0405010.0

(51) Int. Cl.
*A61B 5/00* (2006.01)
*A61F 2/30* (2006.01)
(Continued)

(52) U.S. Cl.
CPC ............ *A61B 5/6878* (2013.01); *A61B 5/103* (2013.01); *A61B 5/1118* (2013.01);
(Continued)

(58) Field of Classification Search
CPC ... A61F 2/28; A61F 2002/3067; A61B 5/6878
See application file for complete search history.

(56) References Cited

U.S. PATENT DOCUMENTS 5,673,367 A * 9/1997 Buckley ................. B25J 9/1612
706/23
6,021,343 A 2/2000 Foley et al.
(Continued)

FOREIGN PATENT DOCUMENTS

WO WO-96/05768 A1 2/1996

OTHER PUBLICATIONS

International Search Report, dated May 31, 2005, 4 pages.
PCT Written Opinion, 7 pages.

*Primary Examiner* — Bruce E Snow
*Assistant Examiner* — Melissa A Hoban
(74) *Attorney, Agent, or Firm* — Mintz Levin Cohn Ferris Glovsky and Popeo, P.C.

(57) ABSTRACT

A method for assessing the orthopaedic performance of a joint of a patient can comprise implanting at least a first and second RF wirelessly detectable markers in first and second bones associated with a site and determining and storing their positions before a surgical procedure is performed. The procedure can be carried out on the site and the positions of the first and second markers can be detected and stored after the procedure has been completed. The detected positions can be used to generate a representation of the orthopaedic performance of the joint after the procedure.

22 Claims, 10 Drawing Sheets

Related U.S. Application Data

(60) Provisional application No. 60/575,395, filed on Jun. 1, 2004.

(51) Int. Cl.
  *A61B 5/11* (2006.01)
  *A61B 5/103* (2006.01)
  *A61B 90/98* (2016.01)
  *A61B 90/00* (2016.01)

(52) U.S. Cl.
  CPC .......... *A61B 5/1121* (2013.01); *A61B 5/1127* (2013.01); *A61B 5/686* (2013.01); *A61B 5/7246* (2013.01); *A61B 5/7445* (2013.01); *A61B 90/98* (2016.02); *A61B 5/0031* (2013.01); *A61B 5/4528* (2013.01); *A61B 5/4571* (2013.01); *A61B 5/4585* (2013.01); *A61B 2090/3916* (2016.02); *A61B 2090/3975* (2016.02); *A61F 2002/3067* (2013.01)

(56) References Cited

U.S. PATENT DOCUMENTS

| | | | |
|---|---|---|---|
| 6,147,480 A | 11/2000 | Osadchy et al. | |
| 6,170,488 B1* | 1/2001 | Spillman, Jr. | A61B 5/0031 128/899 |
| 6,171,239 B1* | 1/2001 | Humphrey | A61B 5/0482 600/372 |
| 6,245,109 B1 | 6/2001 | Mendes et al. | |
| 6,373,240 B1 | 4/2002 | Govari | |
| 6,413,215 B1* | 7/2002 | Wu | A61B 8/08 600/437 |
| 6,424,886 B1* | 7/2002 | Iversen | A61F 2/54 403/128 |
| 6,447,448 B1* | 9/2002 | Ishikawa | A61B 5/0031 128/899 |
| 6,484,118 B1 | 11/2002 | Govari | |
| 6,609,017 B1* | 8/2003 | Shenoy | A61F 2/68 600/372 |
| 6,706,071 B1* | 3/2004 | Wolter | A61F 2/30742 623/22.13 |
| 6,751,492 B2 | 6/2004 | Ben-Haim | |
| 6,968,246 B2* | 11/2005 | Watson | A61F 2/5046 623/23.15 |
| 6,995,729 B2 | 2/2006 | Govari et al. | |
| 7,321,228 B2 | 1/2008 | Govari | |
| 7,397,364 B2 | 7/2008 | Govari | |
| 7,729,742 B2 | 6/2010 | Govari | |
| 7,780,613 B2 | 8/2010 | Sherman | |
| 7,974,680 B2 | 7/2011 | Govari | |
| 8,092,412 B2 | 1/2012 | Sherman | |
| 8,187,213 B2 | 5/2012 | Sherman | |
| 8,244,368 B2 | 8/2012 | Sherman | |
| 2001/0031996 A1* | 10/2001 | Leysieffer | A61N 1/36032 607/57 |
| 2002/0038085 A1 | 3/2002 | Immerz | |
| 2002/0133162 A1 | 9/2002 | Axelson et al. | |
| 2003/0040806 A1* | 2/2003 | MacDonald | A61B 5/4839 623/23.49 |
| 2003/0105470 A1 | 6/2003 | White | |
| 2003/0120150 A1 | 6/2003 | Govari | |
| 2004/0097952 A1 | 5/2004 | Sarin et al. | |
| 2005/0020913 A1 | 1/2005 | Georg et al. | |
| 2006/0047283 A1* | 3/2006 | Evans, III | A61B 5/1076 606/102 |
| 2006/0100498 A1* | 5/2006 | Boyce | A61B 6/505 600/408 |
| 2006/0153978 A1 | 7/2006 | Zhao et al. | |
| 2007/0233267 A1* | 10/2007 | Amirouche | A61F 2/4684 623/20.14 |
| 2008/0294258 A1 | 11/2008 | Revie et al. | |
| 2012/0029345 A1* | 2/2012 | Mahfouz | A61B 5/1036 600/427 |

\* cited by examiner

ORTHOPAEDIC MONITORING SYSTEM, METHODS AND APPARATUS

The present application is a continuation of U.S. application Ser. No. 10/598,600 entitled "Orthpaedic Monitoring System, Methods and Apparatus" filed Aug. 14, 2008, now U.S. Pat. No. 9,380,980, which claims priority to International Application No. PCT/GB2005/000854 entitled "Orthpaedic Monitoring System, Methods and Apparatus" filed Mar. 7, 2005, which claims priority to U.S. Provisional Application No. 60/575,395 entitled "Orthpaedic Monitoring System, Methods and Apparatus" filed Jun. 1, 2004 and to GB Application No. 0405010.0 entitled "Orthpaedic Monitoring System, Methods and Apparatus" filed Mar. 5, 2004, which are hereby incorporated by reference in their entireties.

The present invention relates to apparatus, systems and methods for use in monitoring the performance of a subject, and in particular to apparatus, systems, methods, computer program code and computer program products for use in monitoring the orthopaedic performance of a subject using wirelessly trackable markers.

Markers, also sometimes referred to as fiducial markers, can be used in a number of computer aided surgery ("CAS") and image guided surgery ("IGS") procedures. The positions of the markers can be tracked using a variety of wire based and wireless tracking technologies and the position of an instrument, implant or body part bearing a marker can be controlled or displayed to the surgeon so as to aid the surgeon during the surgical procedure. However, the use of trackable markers is typically limited to during the surgical procedure itself and the markers are typically removed after the surgical procedure.

RSA is a technique for determining the spatial position of a bone in which sets of three lead beads are attached to a patient's bone by a surgical procedure. Two X-rays of the sets of tantalum beads are taken from different directions with the bone in the same position. Knowing the position of the X-ray sources, it is possible to reconstruct the position of the sets of beads in space by projecting back from the two X-ray images of the sets of three beads. However, X-rays can have a deleterious effect on the body and so it is preferable to be able to minimise, reduce or avoid the use of X-rays. Also, this approach requires several pieces of metal to be attached to the body of a patient and it is preferable to reduce or eliminate the exposure of the body to metals, especially toxic metals such as lead. Also the use of X-ray imaging techniques does not provide a highly accurate determination of the position of body parts.

It would therefore be advantageous to be able to accurately monitor the orthopaedic performance of a body in an accurate, and flexible manner which reduces the surgical trauma and other deleterious effects experienced by the body.

According to a first aspect of the present invention, there is provided a method for assessing the orthopaedic performance of a patient. The method comprises attaching a first marker to a first bone and a second marker to a second bone, the bones being associated with a site. A procedure or treatment can be carried out on the site. The positions of the first and second markers can be determined after the procedure has been completed. The detected positions can be used to assess the orthopaedic performance of the patient.

A single marker can be capable of allowing the position and/or orientation of a bone to which it is attached to be determined. Only a single marker can be attached to each bone. Each marker can be uniquely identifiable.

The positions of the markers can be wirelessly detected at radio frequencies. The first and second markers can be wirelessly trackable at radio frequencies;

The markers can be implanted in the bone. The markers can be percutaneously implanted in the bone.

The markers can be attached or implanted before carrying out the procedure. The markers can be attached or implanted before any invasive step associated with the procedure is carried out.

The site can be a joint. Preferably, the site is a knee, hip, shoulder, elbow, foot, hand, or spinal joint. The site can be any body site at which bones or other body structures move relative to one another. The markers can be attached to other body structures as well as bones or instead of bones, including muscles and organs.

The procedure can be a surgical procedure, a clinical procedure, a diagnostic procedure, a therapeutic procedure, a prophylactic procedure, a physiotherapy procedure, a medical procedure, a pharmaceutical administration or dose regime, or any other procedure having or intended to have a remedial, ameliorative or otherwise beneficial effect on the site or the body of the patient.

The patient can be mammalian and can be a human or an animal.

The surgical procedure can be a joint replacement or reconstruction procedure including implanting at least a first prosthetic implant and/or a second prosthetic implant. The joint replacement procedure can be a hip replacement or a knee replacement.

The first prosthetic implant can bear a third marker and the second prosthetic implant can bear a fourth marker. The third and/or fourth marker can be wirelessly trackable at radio frequencies. The method can further comprises wirelessly detecting at radio frequencies the positions of the third and fourth markers after the procedure has been completed.

The first marker can be implanted in the first bone at a first position in the first bone selected to have a minimal movement of the marker relative to the first bone. The second marker can be implanted in the second bone at a second position in the second bone selected to have a minimal movement of the marker relative to the second bone.

The third marker can be at a third position in the first implant and the fourth marker can be in a fourth position in the second implant, wherein the third position and the fourth position each have a fixed separation from a centre of motion of the implants. The centre of motion can be a centre of rotation. The centre of motion can be the centre of rotation of a head part of the first implant in a cup part of the second implant.

The first bone can be the femur and the first position can be the greater trochanter. The second bone can be a part of the pelvis and the second position can be the iliac crest.

Detecting the positions can be carried out with the patient static. Detecting the positions can be carried out with the patient moving. Detecting the positions can be carried out with a load being applied to the site by at least a part of the patient's body under the action of gravity. Detecting the positions can be carried out while loading and/or unloading the site. Detecting the positions can be carried out with the patient standing. Detecting the positions can be carried out with the patient sitting and/or moving between standing and sitting. Detecting the positions can be carried out with the patient walking, jogging or running.

Detecting the positions of the first and second markers after the procedure has been completed can be carried out on a plurality of separate occasions for the same patient and/or for different patients. The detected positions from the plurality of separate occasions to can be used in assessing the orthopaedic performance of the patient.

Assessing the orthopaedic performance of the patient can be used to assess, determine or categorise the effect or success of the procedure on the patient.

The same markers as initially implanted can be detected on the plurality of separate occasions.

The plurality of separate occasions can be at least one month apart. A one of the plurality of separate occasions can be at least one, two, three, fourth, five or six months apart from a preceding occasion. A one of the plurality of separate occasions can be at least one, two, three, fourth, five or six years apart from a preceding occasion. A subset of occasions can be less than a month apart, and/or a further subset of occasions can be at least a month apart but not more than a year apart and/or a yet further subset of occasions can be at least a year apart but not more than ten years apart. The plurality of separate occasions can be at least one year apart.

Using the detected positions to assess the effect of the procedure can include carrying out a qualitative assessment. A qualitative assessment can include considering or comparing the overall form, shape, signature or nature of a representation of the orthopaedic performance derived from the detected positions.

Using the detected positions to assess the effect of the procedure can include carrying out a quantitative assessment. A quantitative assessment can include calculating, determining or deriving a metric which is characteristic of a representation of the orthopaedic performance derived from the detected positions.

Using the detected positions to assess the effect of the procedure includes providing a visual representation and/or a graphical representation of the detected positions. Using the detected positions to assess the effect of the procedure can include providing an animated representation of the patient and/or patient bones and/or implant or implants.

According to a second aspect of the invention, a method for assessing the orthopaedic performance of a patient can comprise implanting a first marker in a first bone and a second marker in a second bone, the first and second markers being wirelessly trackable at radio frequencies. The first bone and the second bone can be on different sides of a joint. The joint can be replaced with a prosthetic joint by implanting a first orthopaedic implant bearing a third marker and implanting a second orthopaedic implant bearing a fourth marker, the third and fourth markers being wirelessly trackable at radio frequencies. The positions of the first, second, third and fourth markers can be wirelessly detected at radio frequencies on a plurality of separate occasions after replacing the joint has been completed. The performance of the prosthetic joint can be assessed using the detected positions of the first, second, third and fourth markers captured on the plurality of separate occasions and using the same markers as initially implanted.

According to a third aspect of the invention there is provided a method for assessing the orthopaedic performance of a patient after procedure has been carried out on a site in the patient. The patient can have a first marker implanted in a first bone and a second marker implanted in a second bone associated with the site. The first and second markers can be wirelessly trackable at radio frequencies. The method can comprise wirelessly detecting at radio frequencies the positions of the first and second markers. The detected positions can be used to assess the orthopaedic performance of the patient.

Preferred aspects and features of the first aspect of the invention can also be preferred aspects of the second and third aspects of the invention, and vice versa.

The site can be a joint. The procedure can have been a surgical procedure. The surgical procedure can have been a joint replacement procedure and the patient can have had at least a first prosthetic implant and a second prosthetic implant. The first and second prosthetic implants can be hip replacement implants or knee replacement implants.

The first prosthetic implant can bear a third marker which is wirelessly trackable at radio frequencies. The second prosthetic implant can bear a fourth marker which is wirelessly trackable at radio frequencies. The method can further comprise wirelessly detecting at radio frequencies the positions of the third and/or fourth markers.

The first marker can be at a first position in the first bone selected to have a minimal movement of the first marker relative to the first bone. The second marker can be at a second position in the second bone selected to have a minimal movement of the second marker relative to the second bone. The first bone can be the femur and the first position can be anywhere along the femur and can be selected from the group comprising: greater trochanter, lesser trochanter; diaphylsis; condyles; tuberosity; and metaphysis. The second bone can be a part of the pelvis and the second position can be any position in the ilium and can be selected from the group comprising: the iliac crest; the acetabulum; and the ischium.

The patient can be static while wirelessly detecting the positions. The patient can be moving while wirelessly detecting the positions. A load can be applied to the site by at least a part of the patient's body under the action of gravity while detecting the positions. The patient can be standing while detecting the positions.

Wirelessly detecting the positions of the first and second markers after the procedure has been completed can be carried out on a plurality of separate occasions. The method can further comprise using the detected positions of the patient or of another patient or patients from a plurality of separate occasions to assess the orthopaedic performance of the patient.

The same markers as initially implanted can be detected on the plurality of separate occasions.

The plurality of separate occasions can be at least one month apart, and can be between one month and six months apart, e.g. two, three, four or five months. The plurality of separate occasions can be at least one year apart, and can be between one year and ten years apart, e.g. two, three, four or five years.

Using the detected positions to assess the effect of the procedure can include carrying out a qualitative assessment and/or a quantitative assessment and/or combining the results of a qualitative and a quantitative assessment or assessments.

Using the detected positions to assess the effect of the procedure can include providing a visual representation or graphical representation of the detected positions.

Using the detected positions to assess the effect of the procedure includes providing an animated representation of the patient and/or the patient's bone or bones and/or the implant or implants.

The animated representation of the patient can include at least a representation or captured image of the first and/or second bones. The animated representation of the patient can include at least a representation or image of a first implant and/or a second implant.

The method can further comprising determining a bone-bone separation from the positions of the first and second markers and/or an implant-implant separation from the positions of the third and fourth markers and/or determining a first implant-bone separation from the positions of the first marker and the third marker or fourth marker and/or determining a second implant-bone separation from the positions of the second maker and the third marker or fourth marker.

The method can include determining a first implant-bone separation from the positions of the first marker and the third marker and determining a second implant-bone separation from the positions of the second maker and fourth marker. The first implant can be implanted in the first bone and the second implant can be implanted in the second bone. The bone-bone separation can be used to assess the kinematic orthopaedic performance of the patient, or the effect of the treatment on the kinematic orthopaedic performance of the patient. The implant-implant separation can be used to assess the performance of the first and second orthopaedic implants. The performance can be the extent of wear of the first and second orthopaedic implants. A first bone-implant separation can be used to assess the performance of the first orthopaedic implant and/or a second bone-implant separation can be used to assess the performance of the second orthopaedic implant. Assessing the performance can include evaluating the likelihood of the first and/or second orthopaedic implant failing.

The quantitative or qualitative assessment, can include a technique or technique selected from the group comprising: comparison with a theoretical model; comparison with the performance of at least another patient or patients; comparison with the previous performance of the same patient.

The quantitative assessment can include a technique or techniques selected from the group comprising: fitting data derived from the detected positions; applying a statistical analysis to data derived from the detected positions; applying a pattern recognition process to data derived from the detected positions.

Assessing the performance can further comprise obtaining a metric from the quantitative analysis or characterising a representation of the orthopaedic performance and using the metric to categorise the orthopaedic performance of the patient. Using the metric can include comparing the metric with threshold or cut-off values. The orthopaedic performance of the patient can be categorised to fall into a category selected from: requiring further periodic orthopaedic assessment; not requiring further orthopaedic assessment; requiring surgical intervention; not requiring surgical intervention; likely to experience implant failure; and not likely to experience implant failure.

According to a fourth aspect of the invention, there is provided an orthopaedic monitoring and/or assessment system for use in assessing the orthopaedic performance of a patient. The system comprises a monitoring station including a tracking system for detecting the position of markers and a computer control system in communication with the tracking system. The computer control system can be configured to determine a marker position for each of a plurality of markers implanted in a patient and to generate an indication of the orthopaedic performance of the patient from the marker positions.

The system can include counterpart features to preferred features and details of the first to third aspects of the invention, and vice versa.

The tracking system can be for detecting markers wirelessly detectable at radio frequencies located within a magnetic field distribution extending over a working volume of the monitoring station. The markers can be wirelessly detectable at radiofrequencies.

The monitoring station can have indicia indicating where a patient should be positioned relative to the monitoring station. The indicia can represent footprints. The footprints can indicate a standing position or positions in which to place the patients feet when walking or running through the station. The monitoring station can include a tread mill or similar device. The monitoring station can include a base on which a patient can be located.

The position of the tracking system, a part of the tracking system, or an antenna bearing part of the tracking system can be adjusted so as to change the position of the working volume at the monitoring station.

The monitoring station can include a support on which a patient can sit. The monitoring station can include a base on which a patient can stand. The monitoring station can include a support which a patient can grasp while standing or sitting. The monitoring station can include three magnetic field generating devices. The magnetic field generating devices can be arranged in a triangular formation. The three magnetic filed generating devices can be arranged in a vertical plane or in a horizontal plane. The three magnetic filed generating devices can be provided as an integral part of the monitoring station or be enclosed within a part of the monitoring station.

The system can further comprise a plurality of markers wirelessly detectable at radio frequencies. Each marker can be hermetically sealed. Each marker can be hermetically sealed in a sealant and/or in a housing. At least one, the or each of the markers can be percutaneously implantable. The or each marker can include a power receiving coil. The monitoring station can transmit a power signal which inductively powers the marker. The or each marker can uniquely identifying itself. The or each marker can indicate its own position and/or orientation in the bone of the patient.

The system can further comprise at least a first orthopaedic implant. The first orthopaedic implant can bear a one of the plurality of markers. The system can comprise a second orthopaedic implant. The second orthopaedic implant can bear a further one of the plurality of markers. The first orthopaedic implant and/or the second orthopaedic implant can provide a hip joint or a knee joint or a part of a hip joint or knee joint.

The indication can be a visual or graphical representation of the orthopaedic performance. The graphical or visual representation can be an animated representation of the patient, a bone or an implant. The indication can be a metric representing the orthopaedic performance. The metric can be characteristic of a representation of the orthopaedic performance derived from the detected positions. The indication can be a categorisation of the patient.

The computer control system can further comprises or have access to a database storing data relating to a previous assessment or assessments of the patient or of other patients. The database can further store data relating to previous assessments of other patients. The database can further store data relating model or theoretical orthopaedic performance, for example, of a bone, joint or implant.

The computer control system can be further configured to distinguish between each of the plurality of markers.

According to a fifth aspect of the invention, there is provided a computer implemented method for assessing the orthopaedic performance of a patient. The method can comprise identifying each of a plurality of markers attached to the patient, determining the position of each of the plurality of markers and generating a representation of the orthopaedic performance of the patient from the positions of the markers.

The method can include counterpart features to preferred features and details of the first to fourth aspects of the invention, and vice versa.

The patient can have a plurality of markers implanted in them. The markers can be wirelessly detectable at radiofrequencies by a tracking system.

The method can further comprise displaying the representation graphically. The method can further comprise assessing the orthopaedic performance of the patient using the representation. The method can further comprise calculating a metric characteristic of, or using, the representation.

Assessing the orthopaedic performance can include carrying out a quantitative analysis of the representation.

Assessing the orthopaedic performance can include comparing a representation of the orthopaedic performance of the patient with at least one representation of the previous orthopaedic performance of the same patient.

Assessing the orthopaedic performance can include comparing a representation of the orthopaedic performance of the patient with at least one representation of the orthopaedic performance of at least one other patient or group of patients, or an average of multiple representations of the orthopaedic performance of at least one other patient or group of patients.

Assessing the orthopaedic performance can include comparing a representation of the orthopaedic performance of the patient with at least one representation of a theoretical or a model orthopaedic performance.

Comparing includes a technique selected from the group comprising: a statistical analysis; data fitting; and pattern recognition. Pattern recognition can include using a neural network. Statistical analysis techniques can include using a chi-squared test, z-test or rank sum test to determine the reliability of a categorisation or assessment of the orthopaedic performance.

The method can further comprise storing data corresponding to the representation in a patient history database for use in a subsequent assessment of the same patient or for use in the assessment of a different patient.

The method can further comprise using at least one of the separation between a first bone and a second bone of the patient, the separation between a bone and an orthopaedic implant of the patient, and the separation between a first orthopaedic implant and a second orthopaedic implant of the patient.

The representation of the orthopaedic performance can be at least one of the separation between a first bone and a second bone of the patient, the separation between a bone and an orthopaedic implant of the patient, and the separation between a first orthopaedic implant and a second orthopaedic implant of the patient.

The representation can be the variation of at least one of the separation between a first bone and a second bone of the patient, the separation between a bone and an orthopaedic implant of the patient, and the separation between a first orthopaedic implant and a second orthopaedic implant of the patient with time. The variation with time can be during a kinematic event, or the variation of the separation for a static event but monitored on different occasions.

According to further aspects of the invention there is provided computer program code executable by a data processing device to provide system according to the system aspect of the invention or a method according to at least one of the method aspects of the invention. A computer readable medium bearing computer program code according to the preceding aspect of the invention is also provided.

An embodiment of the invention will now be described, by way of example only, and with reference to the accompanying drawings, in which.

Figure 1:
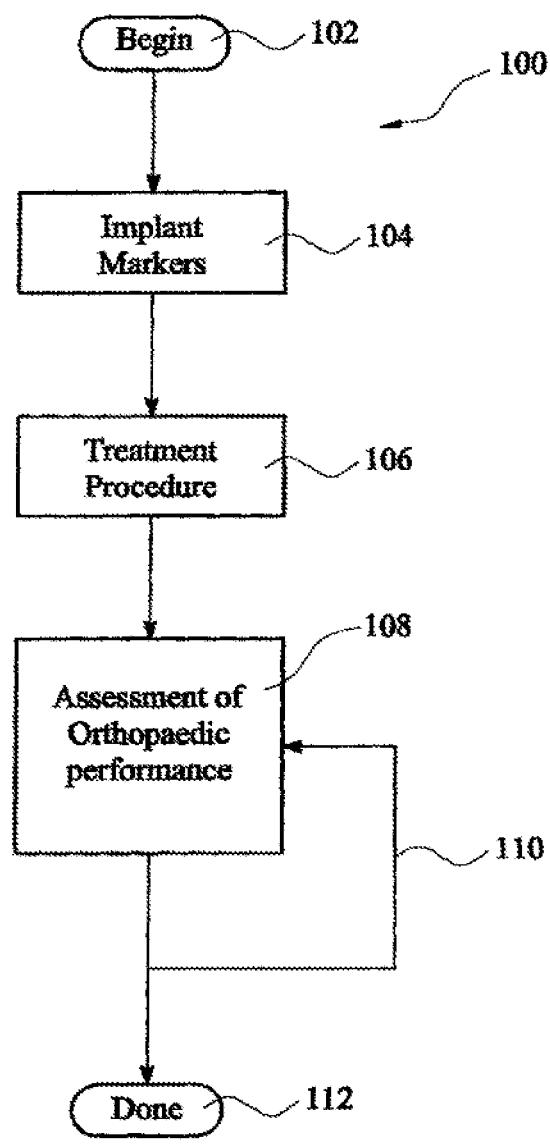
FIG. 1 shows a high level flow chart illustrating an orthopaedic monitoring method according to the invention and including various individual operations according to other aspects of the invention.

Similar items in different Figures share common reference numerals unless indicated otherwise.

With reference to FIG. 1 there is shown a high level flowchart illustrating a general orthopaedic monitoring method 100 according to the invention. Initially an overview of a one of the method aspects of the invention will be provided. The method is particularly suitable for use on a human patient, but can also be used on other mammalian subjects, including animals. The method begins at step 102 and at step 104 markers whose position can be determined by a tracking system are implanted into bones associated with an anatomical structure, such as a joint, where at least two bones move relatively to one another. As used herein, the term orthopaedics is considered to cover both joints and other body structures in which bones move relative to one another. Below, the invention will be described with reference to hip and knee joints, but is not limited to such joints. A marker is implanted in each of the bones associated with a surgical site, e.g. a joint and each of the bones whose position is to be tracked has a marker implanted therein.

Then at step 106, some form of treatment is applied to the surgical site. Various treatments can be carried out, including surgical, clinical, prophylactic and cosmetic procedures. Surgical procedures can include joint replacement procedures using prosthetic implants and can also include procedures not involved in prosthetic implants, e.g. a crucial ligament operation. Also, the procedure need not involve invasive surgery and the procedure can be a physiotherapy type procedure or other non-invasive ameliorative procedure. After the procedure has been completed, at step 108, the orthopaedic performance of the patient, as a result of the treatment carried out at step 106, is assessed at step 108.

The assessment is carried out by determining the positions of the implanted markers in the patient's bones and arriving at some qualitative or quantitative representation of the orthopaedic performance of the patient associated with the treatment site from the positions of the implanted markers. The implanted markers are left in the patient after the treatment has been completed. The implanted markers are also left in the patient after the initial assessment of the patient's orthopaedic performance and at some later date, the patient's orthopaedic performance is assessed again, as indicated by line 110 so as to monitor the patient's orthopaedic performance over a period of time. A first repeat assessment can be carried out after a relatively short period of time, e.g. one month, with subsequent assessments being carried out over longer periods, e.g. every six months. Based on the results of the assessment of the orthopaedic performance, the time between assessments can be varied. For example if there are minor changes between the orthopaedic performance, then future assessments can be carried out less frequently, e.g. every one to five or ten years. Alternatively, if there are significant changes between assessments, then a more frequent assessment regime can be applied, e.g. every few months.

The monitoring of the orthopaedic performance of the patient can be continued for as long as is considered appropriate. If, or when, it is determined that no further monitoring is required, then the monitoring process can cease at step 112. If it is determined that no further monitoring is likely to be required, then the implanted markers can then be removed from the patient. Alternatively, the implanted markers can be kept in the patient in the event that future monitoring and assessment of the patient is required.

Figure 2:
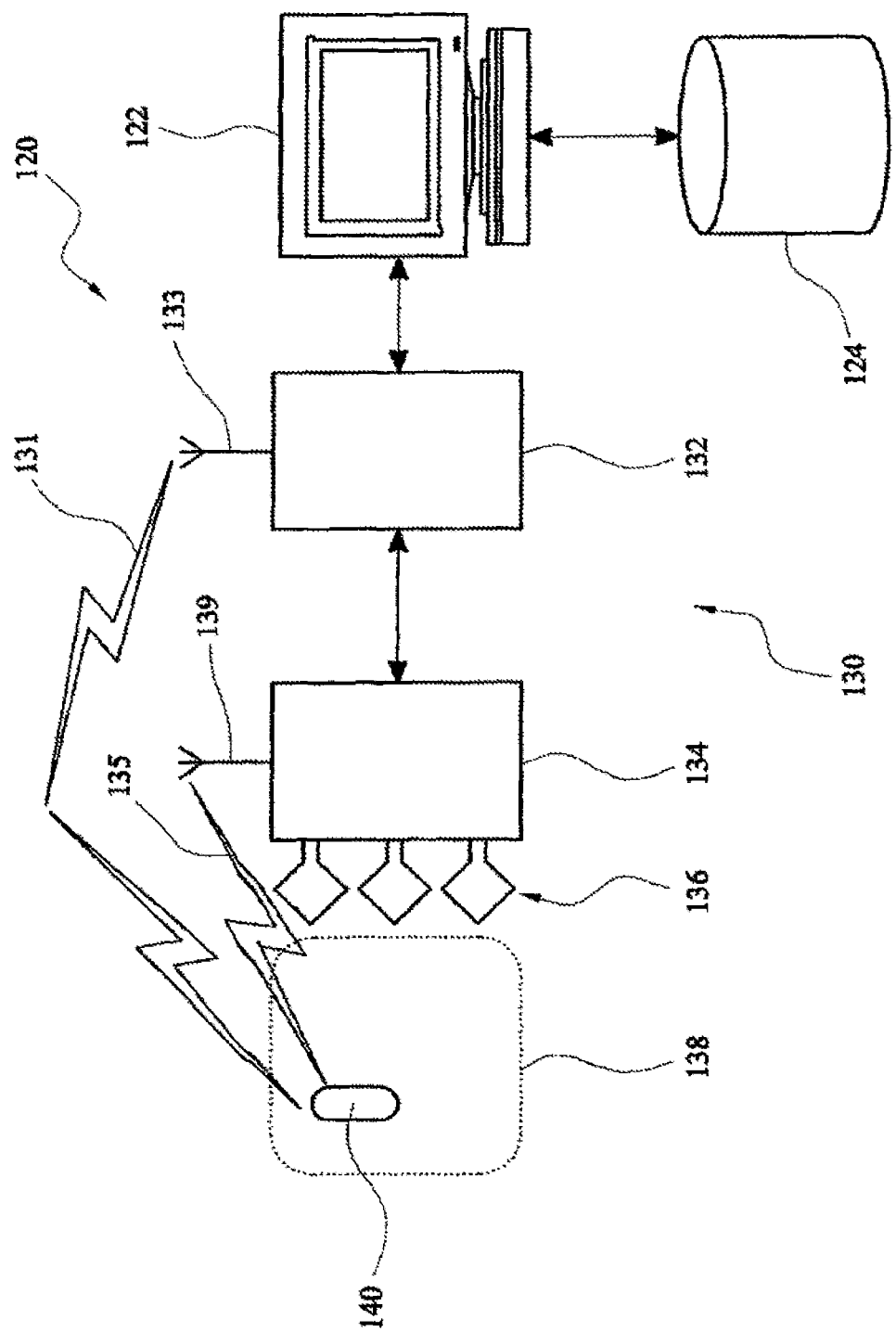
FIG. 2 shows a schematic block diagram of an orthopaedic monitoring system according to the invention.

FIG. 2 shows a schematic block diagram of orthopaedic monitoring system 120 according to the invention and suitable for use in the orthopaedic assessment method 100 according to the invention and corresponding generally to step 108 of the general method 100 described above with reference to FIG. 1. The monitoring system includes wireless tracking functionality as well as orthopaedic assessment functionality. The orthopaedic assessment functionality is generally implemented by a computer 122 carrying out various data processing operations on implant and/or bone positional data items, and other data items, stored in database or databases 124. Hence computer 122 and database(s) 124 provide an orthopaedic assessment sub-system 126. The positional data items are obtained by wirelessly tracking markers located in a patient's bones and/or in prosthetic implants. A wireless tracking sub-system 130 is provided by computer 122, positional signal processing circuitry 132 and monitoring or tracking station 134.

Monitoring station 134 includes three magnetic field generators 136 in the form of coils. The three coils generate a magnetic field distribution 138 which extends over a working volume of the monitoring station. The monitoring station also includes an antenna 139 which wirelessly transmits an electrical power signal 135 at an RF frequency to a marker 140 located within the working volume. Marker 140 wirelessly transmits a signal 131 in which is digitally encoded the position and orientation of the marker and also a unique identifier for the marker. The signal 131 is received by an antenna 133 in communication with the positional signal processing circuit 132.

A suitable marker 140 and associated tracking sub-system 130 for use in the orthopaedic monitoring system 120 will briefly be described in greater detail. Aspects of the marker 140 and tracking sub-system 130 are described in greater detail in U.S. patent publication no. US 2003/0120150 A1 (U.S. patent application Ser. No. 10/029,473) which is incorporated herein by reference in its entirety for all purposes.

The marker, or wireless position sensor, 140, which can be tracked by the tracking sub-system 120, has a housing for the marker which provides a percutaneously implantable marker. As explained above, the marker 140 generates and wirelessly transmits a digital signal 131 encoding data items indicative of the marker's location (x, y and z co-ordinates within the Cartesian reference frame of the tracking system) and orientation (pitch, roll and yaw), in response to the external magnetic field 138 produced by the three field generator coils 136 (also referred to as radiator coils).

Circuitry is present in the monitoring station and further circuitry is present in positional signal processing circuitry. The field generator coils 136 are driven by driver circuits to generate electromagnetic fields at different, respective sets of frequencies $\{w.sub.1\}$, $\{w.sub.2\}$ and $\{W.sub.3\}$. Typically, the sets comprise frequencies in the approximate range of 100 Hz-0 kHz, although higher and lower frequencies may also be used. In one embodiment frequencies in the range of between approximately 15 kHz-0 kHz are used. The sets of frequencies at which the coils radiate are set by a computer 122, which serves as the system controller for tracking sub-system 130. The respective sets of frequencies may all include the same frequencies, or they may include different frequencies. In any case, computer 122 controls driver circuits according to a known multiplexing pattern, which provides that at any point in time, no more than one field generator coil is radiating at any given frequency. Typically, each driver circuit is controlled to scan cyclically over time through the frequencies in its respective set. Alternatively, each driver circuit may drive a respective one of coils 136 to radiate at multiple frequencies simultaneously.

For the purposes of system monitoring station 134, coils 136 may be arranged in any convenient position and orientation, so long as they are fixed in respect to some reference frame, and so long as they are non-overlapping, that is, there are no two field generator coils with the exact, identical location and orientation. Typically, for surgical applications the coils are located in a triangular arrangement. The coil axes may be parallel, or they may alternatively be inclined. Bar-shaped transmitters or even triangular or square-shaped coils could also be useful for such applications.

In orthopaedic and other surgical applications, it is desirable that coils 136 be positioned away from the surgical field, so as not to interfere with the surgeon's freedom of movement. On the other hand, the coils should be positioned so that the working volume 138 of the tracking system includes the entire area in which the surgeon is operating. At the same time, the locations and orientations of coils 136 should be known relative to a given reference frame in order to permit the coordinates of markers 140 to be determined in that reference frame. In practice, coils 136 are mounted on a reference structure part of the monitoring station 134.

The markers 140 include sensor coils, in which electrical currents are induced to flow in response to the magnetic fields produced by field generator coils 136. The sensor coils may be wound on either air cores or cores of magnetic material. Typically, each marker comprises three sensor coils, having mutually orthogonal axes, one of which is conveniently aligned with a principal axis of the housing or of an orthopaedic implant, such as a longitudinal axis. The three coils may be concentrically wound on a single core, or alternatively, the coils may be non-concentrically wound on separate cores, and spaced along the principal axis. The use of non-concentric coils is described, for example, in the PCT Patent Publication WO 96/05768 and in the corresponding U.S. patent application Ser. No. 09/414,875 which are incorporated herein by reference in their entirety for all purposes.

Alternatively, the markers 140 may each comprise only a single sensor coil or two sensor coils. Further alternatively, markers 140 may comprise magnetic position sensors based on sensing elements of other types known in the art, such as Hall effect sensors.

At any instant in time, the currents induced in the sensor coils comprise components at the specific frequencies in sets $\{w.sub.1\}$, $\{w.sub.2\}$ and $\{W.sub.3\}$ generated by field generator coils 136. The respective amplitudes of these currents (or alternatively, of time-varying voltages that may be measured across the sensor coils) are dependent on the location and orientation of the marker relative to the locations and orientations of the field generator coils. In response to the induced currents or voltages, signal processing and transmitter circuitry in each marker generate and transmit signals 131 that are indicative of the location and orientation of the sensor. These signals are received by receiving antenna 133, which is coupled to computer 122 via signal receiver and demodulation circuitry. The computer processes the received signals, together with a representation of the signals used to drive the field generator coils, in order to calculate location and orientation coordinates of the implantable marker. The coordinates are processed and stored by the computer 122 as will be described in greater detail below.

Although tracking sub-system 130 is described as comprising three field generator coils 136, in other embodiments, different numbers, types and configurations of field generators and sensors may used. A fixed frame of reference may be established, for example, using only two non-overlapping field generator coils to generate distinguishable magnetic fields. Two non-parallel sensor coils may be used to measure the magnetic field flux due to the field generator coils, in order to determine six location and orientation coordinates (X, Y, Z directions and pitch, yaw and roll orientations) of the sensor. Using three field generator coils and three sensor coils, however, tends to improve the accuracy and reliability of the position measurement.

Alternatively, if only a single sensor coil is used, computer 122 can still determine five position and orientation coordinates (X, Y, Z directions and pitch and yaw orientations). Specific features and functions of a single coil system (also referred to as a single axis system) are described in U.S. Pat. No. 6,484,118, whose disclosure is incorporated herein by reference.

When a metal or other magnetically-responsive article is brought into the vicinity of an object being tracked, the magnetic fields in this vicinity are distorted. There can be a substantial amount of conductive and permeable material in a surgical environment, including basic and ancillary equipment (operating tables, carts, movable lamps, etc.), as well as invasive surgery apparatus (scalpels, scissors, etc.). The magnetic fields produced by field generator coils 136 may generate eddy currents in such articles, and the eddy currents then cause a parasitic magnetic field to be radiated. Such parasitic fields and other types of distortion can lead to errors in determining the position of the object being tracked.

In order to alleviate this problem, the elements of the monitoring station 130 and other articles used in the vicinity of the monitoring system are typically made of non-metallic materials when possible, or of metallic materials with low permeability and conductivity. In addition, computer 122 may be programmed to detect and compensate for the effects of metal objects in the vicinity of the monitoring station. Exemplary methods for such detection and compensation are described in U.S. Pat. Nos. 6,147,480 and 6,373,240, as well as in U.S. patent application Ser. No. 10/448,289, filed May 29, 2003 and Ser. No. 10/632,217 filed Jul. 31, 2003, incorporated herein by reference.

The marker in this embodiment comprises three sets of coils: sensor coils, power coils, and a communication coil. Alternatively, the functions of the power and communication coils may be combined, as described in U.S. patent application Ser. No. 10/029,473. The coils are coupled to electronic processing circuitry, which is mounted on a suitable substrate, such as a flexible printed circuit board (PCB). Details of the construction and operation of the circuitry are described in U.S. patent application Ser. No. 10/029,473 and in U.S. patent application Ser. No. 10/706,298 which are incorporated herein by reference in their entirety for all purposes.

Marker 140 can include only a single sensor coil and a single power coil 144, but in practice sensor 140 typically comprises multiple coils of each type, such as three sensor coils and three power coils. The sensor coils are wound together, in mutually-orthogonal directions, on a sensor core, while the power coils are wound together, in mutually-orthogonal directions, on a power core. Alternatively, the sensor and power coils may be overlapped on the same core, as described, for example in U.S. patent application Ser. No. 10/754,751, filed Jan. 9, 2004 whose disclosure is incorporated herein by reference. It is generally desirable to separate the coils one from another by means of a dielectric layer (or by interleaving the power and sensor coils when a common core is used for both) in order to reduce parasitic capacitance between the coils.

In operation, power coils serve as a power source for sensor 140. The power coils receive energy by inductive coupling from external driving antenna 139 attached to RF power driving circuitry. Typically, the driving antenna radiates an intense electromagnetic field at a relatively high radio frequency (RF), such as in the range of 13.5 MHz. The driving field causes currents to flow in power coils, which are rectified in order to power the circuitry. Meanwhile, field generator coils 136 induce time-varying signal voltages to develop across the sensor coils as described above. The circuitry senses the signal voltages, and generates output signals in response thereto. The output signals may be either analog or digital in form. The circuitry drives the communication coil to transmit the output signals to receiving antenna 133 outside the patient's body. Typically, the output signals are transmitted at still higher radio frequencies, such as frequencies in the rage of 43 MHz or 915 MHz, using a frequency-modulation scheme, for example. Additionally or alternatively, the coil may be used to receive control signals, such as a clock signal, from a transmitting antenna (not shown) outside the patient's body.

As explained above, the driver circuitry also comprises an RF power driver, which drives antenna 139 to emit power signal 135, preferably in the 2-10 MHz range. The power signal causes a current to flow in power coil, which is rectified by circuitry and used to power the markers internal circuits. Meanwhile, the electromagnetic fields produced by field generator coils 136 cause currents to flow in the sensor coil. This current has frequency components at the same frequencies as the driving currents flowing through the generator coils 136. The current components are proportional to the strengths of the components of the respective magnetic fields produced by the generator coils in a direction parallel to the sensor coil axes. Thus, the amplitudes of the currents indicate the position and orientation of the sensor coils relative to fixed generator coils 136.

The circuitry measures the currents flowing in the sensor coils at the different field frequencies. It encodes this measurement in a high-frequency signal, which it then transmits back via an antenna to antenna 133. The circuitry comprises a sampling circuit and analog/digital (A/D) converter, which digitizes the amplitude of the current flowing in the sensor coils. In this case, the circuitry generates a digitally-modulated signal, and RF-modulates the signal for transmission by the antenna. Any suitable method of digital encoding and modulation may be used for this purpose. The circuitry also stores a unique identifier for each marker and similarly generates a digitally-modulated signal, and RF-modulates the signal 131 for transmission by the antenna. Other methods of signal processing and modulation will be apparent to those skilled in the art.

The digitally-modulated signal transmitted by the antenna is picked up by a receiver, coupled to antenna 133. The receiver demodulates the signal to generate a suitable input to signal processing circuits which can be separate to, or integrated in, the computer system 122. Typically, the receiver amplifies, filters and digitizes the signals from marker 140. The digitized signals are received and used by the computer 122 to compute the position and orientation of marker 140. General-purpose computer 122 is programmed and equipped with appropriate input circuitry for processing the signals from the receiver.

Preferably, the receiver circuitry includes a clock synchronization circuit, which is used to synchronize the driver circuits and RF power driver. The RF power driver can operate at a frequency that is an integer multiple of the driving frequencies of field generators 136. The marker circuitry can then use the RF signal received by the power coil not only as its power source, but also as a frequency reference. Using this reference, marker circuitry is able to apply phase-sensitive processing to the current signals generated by the sensor coils, to detect the sensor coil currents in phase with the driving fields generated by coils 136. The receiver can apply phase-sensitive processing methods, as are known in the art, in a similar manner, using the input from the clock synchronization circuit. Such phase-sensitive detection methods enable marker 140 to achieve an enhanced signal/noise (S/N) ratio, despite the low amplitude of the current signals in the sensor coils.

Although certain frequency ranges are cited above by way of example, those skilled in the art will appreciate that other frequency ranges may be used for the same purposes.

Marker circuitry also stores a unique identifier for marker 140 and the unique identifier is also transmitted to the tracking sub-system 130, so that the tracking sub-system can determine the identity of the marker from which positional data is being received. Hence the tracking sub-system can discriminate between different markers when multiple markers are present in the working volume 138 of the monitoring station.

An advantage of using wireless markers, such as marker 140, without an on-board power source, is that the markers can be inserted in and then left inside the patient's body for later reference.

The marker can be hermetically sealed by encapsulation in a sealant or encapsulant. Preferably the sealant provides any, some or all of the following shielding properties: mechanical shock isolation; electromagnetic isolation; biocompatibility shielding. The sealant can also help to bond the electronic components of the marker together. Suitable sealants, or encapsulants, include USP Class 6 epoxies, such as that sold under the trade name Parylene. Other suitable sealants include epoxy resins, silicon rubbers and polyurethane glues. The marker can be encapsulated by dipping the marker in the sealant in a liquid state and then leaving the sealant to set or cure.

Marker 140 can be attached to orthopaedic prosthetic implants so as to allow the position of the orthopaedic implants to be tracked. A housing can be provided around the encapsulant and then the housed marker can be secured to the orthopaedic implant. Embodiments of particular replacement hip and knee orthopaedic implants are described in greater detail below with reference to FIGS. 3 and 4.

A housing can be provided for the marker which can provide an implantable marker which can be implanted directly in the bone of the patient. In a preferred embodiment, the implantable marker is configured to be "injectable" through the skin of the patient without requiring an ancillary incision or other preliminary surgical procedure. The housing has a generally cylindrical body having a tapered distal end and a screw thread extending along the longitudinal axis of the housing. A connector in the form of a generally square shaped formation is provided at the proximal end for releasably engaging with an insertion instrument so as to impart rotational drive to the housing so that the implantable marker can be screwed into the patient's bone. In one embodiment, the housing has a sharp, skin piercing tip at the distal end with a self-tapping screw thread thereon. The implantable marker can then be percutaneously implanted into the bone by pushing the marker through the skin, optionally using a guide instrument having a guide tube with a guide channel passing there along, and then screwing the implantable marker into the bone.

In another embodiment, no screw thread is provided and the outer surface of the housing is substantially smooth and the distal end has a sharp bone penetrating tip, such as a trochanter tip. In this embodiment, the implantable marker can be percutaneously implanted by driving the implantable marker through the skin and pushing the implantable marker into the bone. While the screw thread provides a bone anchor for some embodiments, in this embodiment, barbs, ribs or other surface features can provide a bone anchor. Alternatively, a bone anchor can be provided by treating the outer surface of the marker housing to encourage, facilitate or otherwise promote bone on growth. For example the outer surface of the housing can be roughened or chemically treated.

In a further embodiment, the housing includes a non-bone penetrating tip or nose, made of a resorbable material. Prior to implanting the marker, a hole is drilled in the bone using a guide tube and then the implantable marker is guided towards the pre-drilled hole by the guide tube and the tip self locates the implantable marker in the pre-drilled hole and then the implantable marker is screwed into the pre-drilled hole so as to drive the implantable marker into the bone.

A monitoring station 134 is provided according to the present invention. The monitoring station includes a base part on which a patient stands in use. Guide rails can optionally be provided on which a patient can grasp by their hands in use. The guide rails also serve to guide the motion of a patient through the monitoring station. The monitoring station also includes a band or support member on which a support frame is moveably mounted. Support frame also includes three field generator coils arranged in a generally triangular configuration and in a vertical plane.

The position of the field generator coils can be adjusted in the vertical and horizontal directions (and also in the third transverse direction) so as to change the position of the working volume 138 of the monitoring station.

An upper surface of base can include first and second foot marks which provide indicia indicating the preferred position for a patient to stand at the monitoring station. A second set of foot marks can also be provided to indicate the preferred positions for a patient to place their feet while walking across the base 180 during a dynamic or kinematic monitoring process.

A further embodiment of the monitoring station 134 can includes a seat which provides a support on which the patient can sit. A kinematic or dynamic assessment can include monitoring the position of the implants as the patient moves from a standing to a sitting position and vice versa so as to assess the performance of the patient's joints during the loading and unloading of the joints under the person's weight. Monitoring station 134 can include a guide bar graspable by a person to provide support, if required. The position of the guide bar can be altered by inserting free ends of the guide bar into a series of holes provided in the base. Computer control system 132 is provided separately to the monitoring station 134 on a trolley which also holds signal processing electronics 132. In this embodiment of the monitoring station, the field generator coils 136 are provided in a triangular configuration within the base and in a generally horizontal configuration. The working volume 138 extends upwardly from the base.

The use of orthopaedic monitoring system 120 in the orthopaedic performance assessment method will now be described in greater detail. A method corresponding generally to method 100 will now be described in greater detail. The method will be described in the context of carrying out a hip replacement or knee replacement surgical procedure but is not limited to such procedures or to surgical procedures alone.

The method begins and at a first step an implantable marker is percutaneously implanted in a bone to either side of the joint. The implantable markers should be implanted at specific positions in the bones so as to minimise or prevent the movement of the implantable markers in the bone. By preventing minimising the movement of the implantable markers in the bone, the accuracy of the assessment method is improved. The positioning of the implantable markers will be described in greater detail below with reference to FIGS. 3 and 4. Prior to beginning the method, the joint of the patient is preferably scanned, to collect body image data, e.g. using CT, X-ray or fluoroscopic x-ray, so as to provide images of the bone for use during the surgical procedure. Preferably the implantation of the markers is carried out using a navigated or image guided procedure in which the image of the bone is displayed together with a representation of the position of the implantable marker which is tracked by a tracking system similar to that described above. In this way, the accuracy of positioning of the implantable markers in a percutaneous fashion, is improved.

After the implantable markers have been implanted, the images of the bone are registered with the markers so that the bone images are registered in the reference or co-ordinate frame of the tracking system. A number of techniques can be used to register the body image data in the frame of reference of the tracking system. An X-ray or CT scan based registration method can be used.

In general, the position of the images of the body in the reference frame of the tracking system can be determined using a marker detectable by the tracking system. As the position of the marker in the reference frame of the tracking system is known and the position of the body part which has been imaged is known in the reference frame of the tracking system, the position of the image in the reference frame of the tracking system relative to the body part can be determined and so the images can be brought into registration with the body part in the reference frame of the tracking system.

Non-image based registration techniques can also be used. For example, a marker detectable by the tracking system can be attached to the bone so that the position of the bone in the reference frame of the tracking system is known. Then a plurality of points on the surface of the bone are identified and captured by the tracking system (in a process sometimes referred to as digitisation). The plurality of points typically extend over an anatomical feature having a characteristic shape or geometry. Then a model or other virtual representation of the bone, is morphed and scaled to coincide with the captured positions and the transformed model of the bone is then considered to correspond to the actual bone. Hence the position of the actual bone in the reference frame of the tracking system is known and so the bone position is registered with the tracking system.

After the markers have been registered with the bones, some pre-operative diagnostic actions can optionally be carried. The pre-operative diagnostics can be carried out using the monitoring station 134 to capture the position of the implanted markers and hence determine the position of the patient's bones as the patient undergoes a number of exercises or activities so as to allow the pre-operative performance of the joints to be assessed. For example the positions of the bones in standing and sitting positions, and transitioning between the two can be captured. The bone positions of the patient as the patient walks can be captured and used in a gait analysis. Other patient's activities can be carried out and the positions of the bones tracked in order to further assess the performance of the joints. The physiological status of the patient over the entire range of motions and joint articulations can be assessed. For example, the positions of the bones under different load bearings and at abduction, adduction, flexion, extension, inversion and aversion configurations of the joints. Also the articulation surface or surfaces of the joints can be assessed.

After completion of the pre-operative diagnostic steps, the surgical procedure is carried out. Preferably the surgical procedure is a navigated surgical procedure in which a tracking system and markers on various tools, instruments and implants are used together with an image guided surgical system which provides a visual representation of the positions of the bones, implants and tools to assist the surgeon in correctly positioning the implants.

Figure 3:
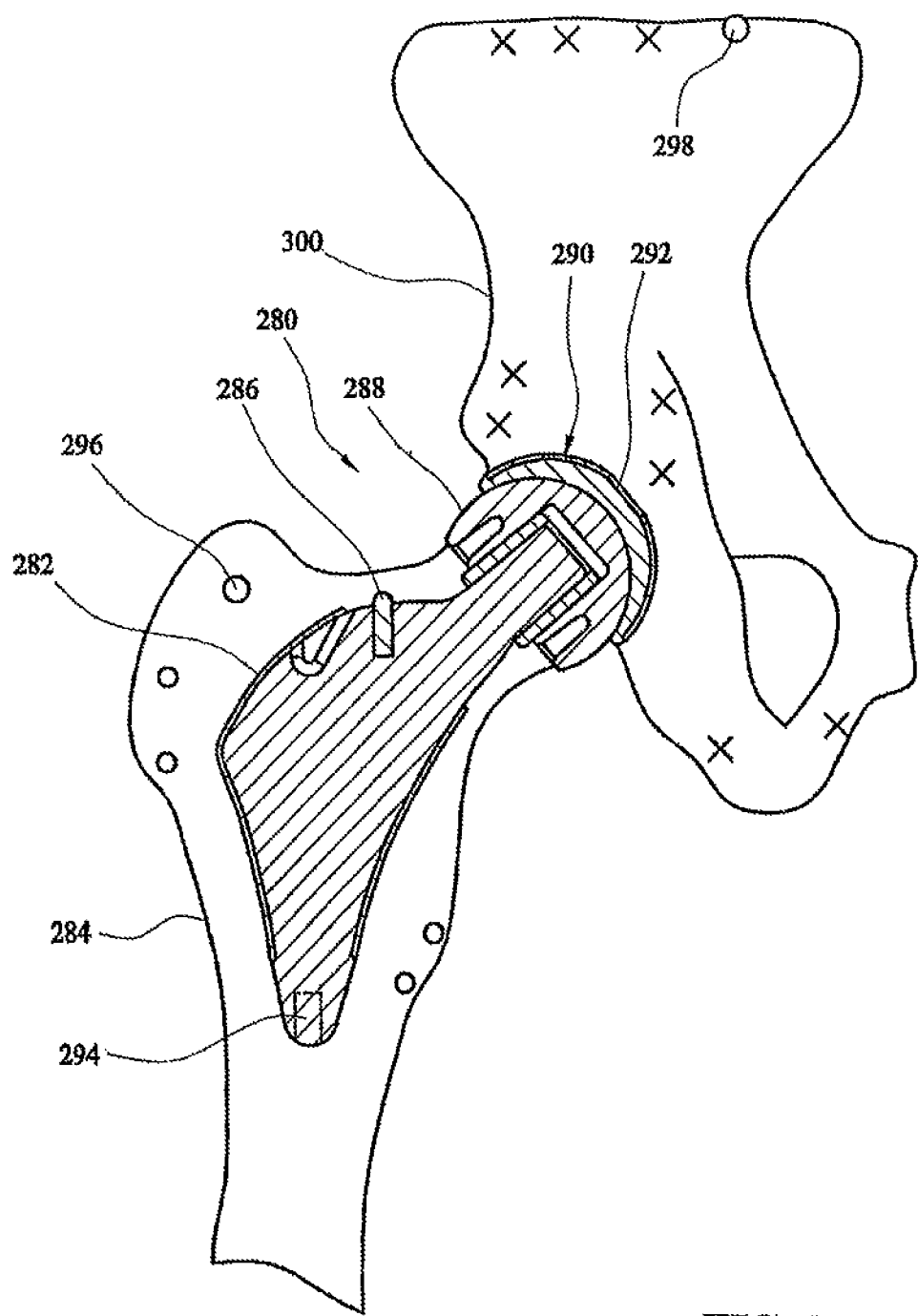
FIG. 3 shows a cross sectional view through a monitorable hip of a patient including trackable hip replacement implants.

FIG. 3 shows a total hip joint replacement prosthetic implant 280 as implanted at the hip of a patient. The implant 280 includes a first femoral component 282 which is implanted towards the top of the femur 284. Femoral implant component 282 includes a marker 286 securely attached to the implant. The longitudinal axis of the implant is substantially parallel to or co-linear to the axis of the stem of the implant 282 and the marker 286 has a known positional relationship to the centre of rotation of the head part 288 in the acetabular cup 290. Cup 290 also includes a marker 292, similar to marker 140 but having a more planer configuration. Marker 292 also has a known spatial relationship with the centre of rotation of head 288 in cup 290. In alternate embodiment, marker 286 can be located at position 294 toward the bottom of the stem of the femoral implant 282.

A first implantable marker 296 was implanted near the greater trochanter of the femur 284. This position helps to avoid interference with instruments and helps increase accuracy. Other suitable sites in the femur for marker 296 are indicated by o's in FIG. 3. Suitable sites can also include the condyles, the femoral shaft distal to the stem and the metaphysis. A second implantable marker 298 was implanted near the acetabulum of the pelvis 300. A preferred location for the second implantable marker is in the iliac crest of the pelvis. This position helps to avoid interference with instruments and helps increase accuracy. Other sites can include the acetabulum, ischium and pubis. Other suitable sites for implanting marker 298 in the pelvis are indicated by x's in FIG. 3.

As mentioned above, in order to enhance the accuracy of the assessment method, the bone markers should be implanted at positions in the bone at which the markers will not move significantly relative to the bone. It is also beneficial to have the bone markers as close to each as possible to improve the accuracy of the assessment. Preferably the markers are within approximately 20 cm of each other. It is also desirable to have the bone markers subjected to as little stress as possible during the lifetime of the implantation of the markers in the patient. The bone markers should be implanted in regions having low bone mineral density changes. The bone markers should be implanted in regions having low bone mineral density changes. Preferably the bone implantation site has a bone mineral density change of less than 40%. The bone marker implantation site preferably moves by less than 0.2 mm per year.

For example, the iliac crest of the pelvis tends to undergo small changes in bone mineral density and therefore is a suitable site for implanting the pelvic bone marker. The greater trochanter and lesser trochanter of the femur also typically undergo small changes in bone mineral density and therefore provide suitable sites for the femoral marker 296. The positions for implanting the bone markers are selected so as to try and minimise any changes in position of the bone markers, owing to movement of the bone itself. In that way, changes in the position of the bone markers relative to each other or relative to the implant positions are more reliably identifiable.

Figure 4:
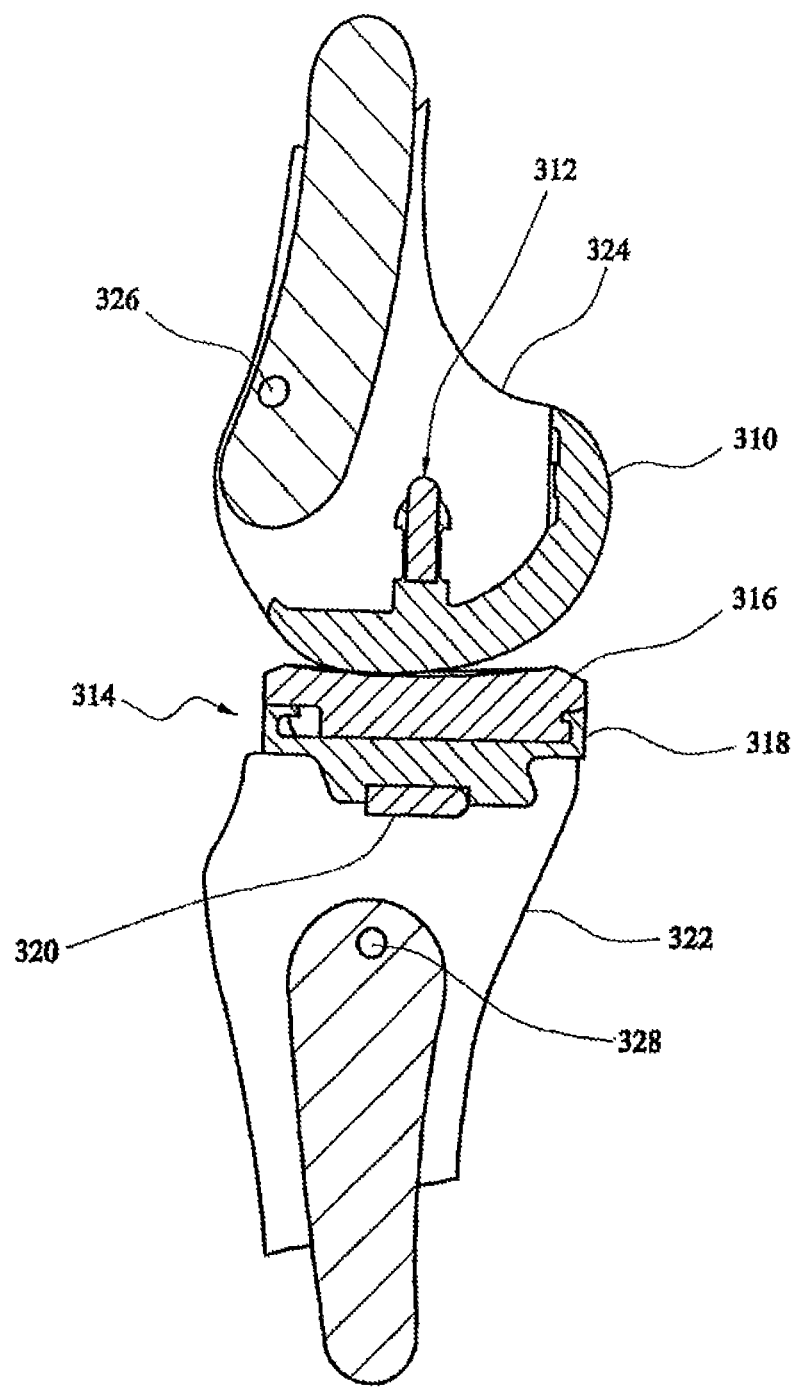
FIG. 4 shows a cross sectional view through a monitorable knee of a patient including trackable knee replacement implants.

FIG. 4 shows a cross-sectional view through a knee, illustrating a total knee replacement. A femoral implant 310 bears a marker 312 similar to marker 140. A tibial implant 314 includes an upper bearing component 316 and a tibial tray component 318 bearing a marker 320 similar to marker 140. Tibial implant 314 is attached to the upper end of tibia 322 and femoral implant component 310 is attached to the lower end of femur 324.

Similar considerations to the positioning of femoral and tibial bone markers apply as to those discussed above with regard to the hip joint. Again, the objective is to minimise movement of the marker in the bone so that any changes in marker position are owing to changes in the performance of the joint, rather than inherent movement of parts of the bone. A suitable position for implanting the femoral bone marker 326 would be at the position indicated in FIG. 4, although other positions within the shaded region of the femur shown in FIG. 4 would be suitable also. Positions closer to the femoral implant are preferred. A preferred position for the femoral bone marker is in the condyles and approximately 5 cm from the joint line. This position helps to reduce interference with instruments and increase accuracy. Other positions can include the femoral shaft (diaphysis) and the greater trochanter. A suitable position for implanting the tibial bone marker 328 would be at the position indicated in FIG. 4, although other positions within the shaded region of the tibia shown in FIG. 4 would be suitable also. Positions closer to the tibial implant are preferred. A preferred position for implanting the tibial bone maker is in the condyles approximately 5 cm from the joint line. This position helps to reduce interference with instruments and increase accuracy. Other positions can include the tuberosity, the shaft and the malleous.

After the navigated implantation of the hip and/or knee prosthetic implants has been completed, the position of the implants is registered with the reference frame of the tracking system. The orthopaedic implant markers are also wirelessly powered and the orthopaedic implant markers are powered up and the tracking system 130 detects the position of the markers in the implants and the positions of the implants in the reference frame of the tracking system is determined. After the implants have been registered with the tracking system, an initial assessment of the orthopaedic performance of the patient can be carried out immediately after the operation. For example, the patient can be brought to or enter the monitoring station and the position of the bones and implants can be detected and the position of the bones and implants can be displayed on the screen of computer 122 so that the positioning of the implants can be assessed.

The orthopaedic performance of the patient can be statically or dynamically assessed, including varying the loading of the joints by the patient standing and sitting and by the patient walking or running through, or at the monitoring station, e.g. on a tread mill or similar. The position data for the orthopaedic implants and for the bones is captured and stored by computer system 122 as will be described in greater detail below. This initial positional data of the implants and bones can provide a "base line" against which the future orthopaedic performance of the patient can be gauged. Alternatively, this initially collected data can be used to assess the success of the surgical procedure in positioning the orthopaedic implants to provide the desired kinematic performance of the patient's joints.

In particular, the separation between the bone implants associated with the joint is determined and stored. Also the separation between the orthopaedic implant markers is determined and stored. Also, the separation between a bone marker and orthopaedic implant marker, e.g. the femoral bone marker and femoral implant marker and the separation between the pelvic bone marker and cup marker are also determined and stored. In other embodiments, the separation between a bone marker and the implant in the other bone can also be determined and stored, e.g. the separation between the femoral bone marker and the cup implant marker and the separation between the pelvic bone marker and the femoral implant marker. Similar bone-bone, implant-implant and bone-implant separations can also be determined and stored for the knee joint.

After the immediate post-operative assessment, the orthopaedic performance of the patient can be assessed again using the monitoring station. The monitoring station is used to capture bone marker and implant marker positional data which is processed by computer system 122 to allow the orthopaedic performance of the patient to be assessed as will be described in greater detail below. The first diagnosis can be any suitable period after the operation, such as a few weeks or a month. As a result of the assessment step, it may be determined that there is a significant problem with the results of the surgical procedure. For example, the results of the assessment may be that an implant is loose or that an implant is incorrectly positioned or that the orthopaedic behaviour of the patient is otherwise improper. Therefore a determination can be made whether a remedial or other corrective act should be taken based on the assessment. If it is determined that, for instance an implant is becoming loose, then the patient can be subjected to a corrective or remedial treatment such as replacing the implant or otherwise correcting the deficiency identified by the assessment. After the treatment has been completed, the monitoring of the patient can be considered to be completed or alternatively, the method can return to the registration or post-operative assessment step, as appropriate and the effect of the treatment step on the orthopaedic performance of the patient can be continued to be monitored.

If it is determined that no remedial or corrective treatment is required, then it can be determined whether the assessment of the patient's orthopaedic performance indicates that the orthopaedic implant or other surgical procedure has become sufficiently stabilised that there are no noticeable ongoing changes in the patient's orthopaedic performance. If it is determined that further monitoring should be carried out, then the patient can return for a further assessment after a further period of time, e.g. several months to a year or several years. Hence the orthopaedic performance of the patient is periodically assessed so as to monitor the patient's orthopaedic performance. It will be appreciated that the bone markers and orthopaedic implant markers are left in the patient. These markers are the same markers as were initially implanted at the first step.

It may be determined, that there appears to be little likelihood that there will be any further significant changes in the orthopaedic performance of the patient. If it is, then the bone markers can be removed. It can be preferably to minimise the amount of foreign material present in a patient's body. Once the bone markers have been removed, then the monitoring of the orthopaedic performance can cease. If accessible, the orthopaedic implant markers can also be removed or alternatively they can be retained, if not accessible for removal. Hence the orthopaedic performance based on the positions of the orthopaedic implants in the body can still be monitored, if deemed appropriate.

If after the bone markers and/or orthopaedic implant markers have been removed, the patient suffers a change in orthopaedic performance, e.g. starts to experience hip or knee pain, then the markers can be re-implanted and the periodic assessment regime, corresponding generally to step 108, can be re-started. However, it is envisaged that using the markers and implants described herein, long term monitoring, for example up to 25 years, or longer can be realised.

Figure 5:
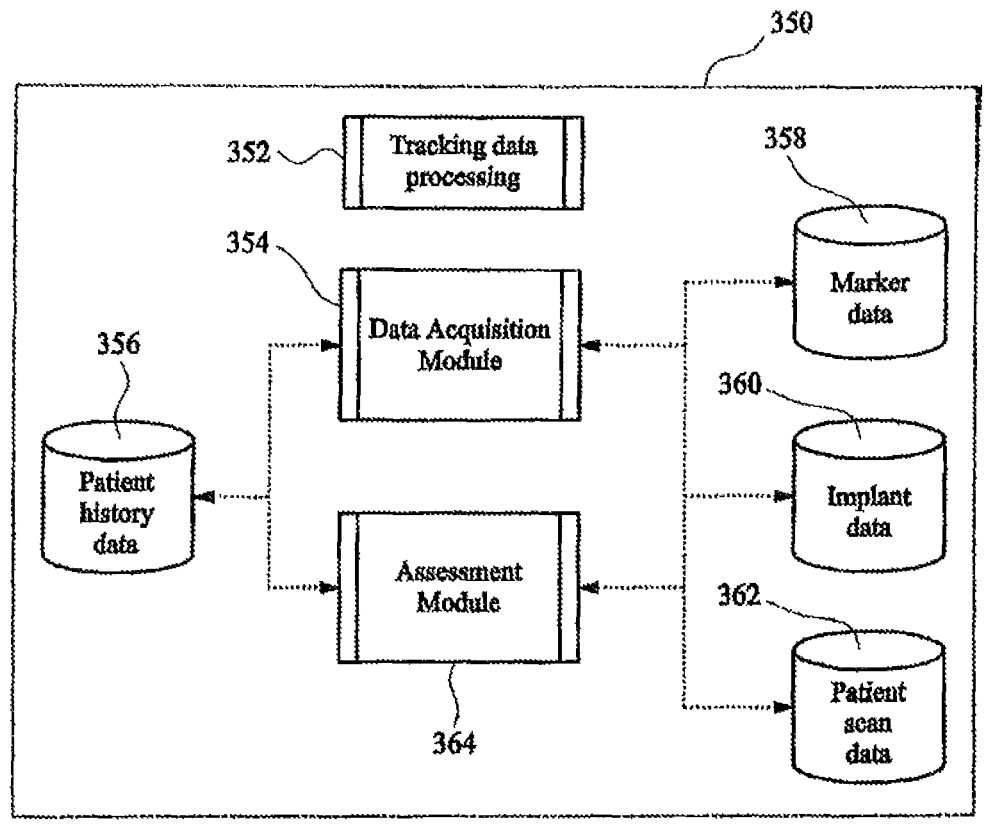
FIG. 5 shows a schematic software architecture for a computer implemented control part of the system shown in FIG. 2 according to the invention.

With reference to FIG. 5, there is shown a software architecture 350 of computer system 122. Computer system 122 includes an operating system under which various applications can execute, including surgical navigation, planning and image guided surgery applications which can be used to plan and carry out the orthopaedic implant surgical procedures. Software architecture 350 focuses on the software entities of particular relevance to the orthopaedic monitoring and assessment method of the present invention.

A software module for processing tracking data, signals and information received from the tracking system 130 is provided. The tracking module 352 determines the position of the markers within the reference frame of the tracking system and also extracts the marker identified data items which are passed or otherwise made available to the other software modules. The tracking module also handles the generation of control signals and processing of other signals from the tracking system so as to control its general tracking functionality.

Computer system 122 also includes a software module which handles the acquisition of bone and implant positional data from patients at the monitoring station. The positional data acquisition module 354 interacts with the tracking system module 352 and processes the marker ID and marker positional data and reads and writes to various parts of database 124.

As illustrated in FIG. 5, database 124 includes a number of databases or tables within the same database, including a patient's history database 356, a marker database 358, an implants database 360 and a patient scan database 362. Separate databases are illustrated in FIG. 5 for the sake of clarity and explanation only, and a single database or other arrangements of the data items stored can be used. The data items have stored and organised by database 124 will be described in greater detail below with reference to FIG. 6.

Computer system 122 also includes an assessment module which processes the data captured and stored by the data acquisition module 354 in order to provide an assessment of the orthopaedic performance of the patient. The operation of computer acquisition module 354 is described in greater detail with reference to FIG. 7. The functionality of diagnosis and assessment module 364 is described in greater detail with reference to FIG. 8 below.

Figure 6:
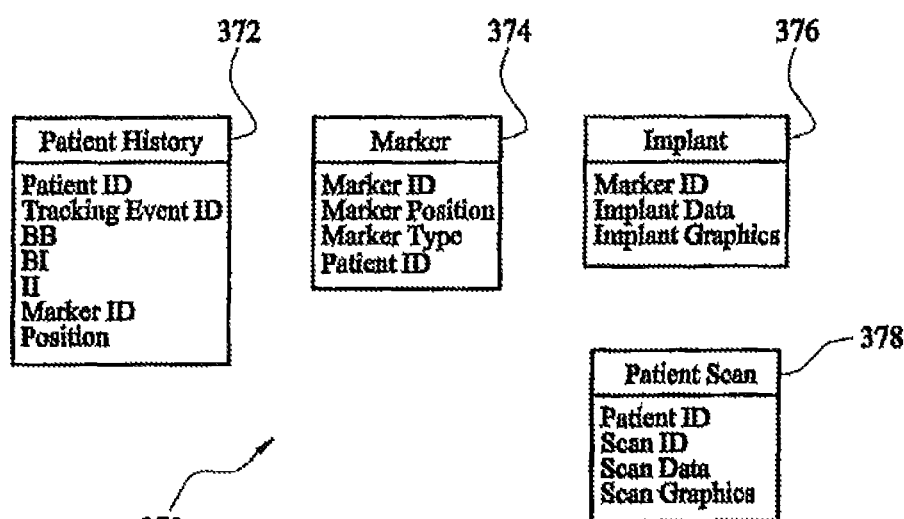
FIG. 6 shows a database schema for the database(s) of the software architecture.

FIG. 6 shows a database schema 370 for database 124. The embodiment illustrated in FIG. 6 includes four tables. A first patient history table 372 stores various data items relating to prior and current monitoring of the orthopaedic performance of a patient. The table includes a patient ID field which stores a data item uniquely identifying a patient. A tracking event ID field is also provided which stores a data item uniquely identifying each patient's orthopaedic assessment even that has been tracked by the tracking system at the monitoring station. A field is provided for storing a data item indicating the bone and bone separation for a joint. A BI field or fields are provided for storing bone implant separations for a joint. An II field or fields are provided for storing implant-implant separations for a joint. A marker ID field is provided for storing a unique identifier for each marker associated with the joint and a position field is provided storing data representing the captured position of the marker corresponding to the marker ID. Hence both the "raw" marker position data is available for each tracking event together with a representation of the joint performance, derived from the positional data, such as the bone-bone, bone-implant and implant-implant separation data items.

A marker table 374 stores various data items relating to each of the wirelessly detectable markers that the tracking system can interact with. A marker ID field stores a data item representing a unique identifier for each trackable marker. Before a marker can be recognised by the system, an administrator can update the marker table 374 with various information relating to the marker, including the marker's unique identifier. A marker position field is provided which stores the registered position of the marker in the reference frame of the tracking system. A marker type field is provided for storing a data item indicating the type of the marker, e.g. the type of bone marker or whether the marker is an orthopaedic implant marker. A patient ID field is also provided storing the unique identifier of the patient in which the marker has been implanted. Again, this data item is updated by an administrator.

In one embodiment, the marker part of the implantable marker also includes a transducer or other sensor for detecting a property in the region or area around where the marker has been implanted. The transducer or sensor generates an electrical signal representative of the local property of the body and the signal is processed by circuitry for transmission back to the tracking system using an antenna. In other embodiments, the signal from the transducer can be transmitted back to the tracking system using a wire line system, e.g. a electrical conductor or optical conductor, such as a fibre optic cable.

By looking up the marker type associated with the transmitted marker ID, the system can determine what the type of the local property signal being transmitted and handle it accordingly. For example, the system may determined that the marker ID is associated with a temperature marker type in which case the system can determine that it is also receiving temperature data or information which can be processed and handled accordingly.

The transducer or sensor can be of many types, depending on the property to be measured. For example the body transducer can be a pressure transducer which provide a measure of the local stress, a temperature sensor, which provides a measure of the local temperature, a biological activity sensor, which provides an indication of a biological activity (e.g. osteoblast activity) or a chemical sensor, which provides an indication of a local chemical property (e.g. pH). Other types of sensors for different kinds of properties can of course be used also. A marker type data item is provided associated with each kind of property.

An implant table 376 stores data items relating to orthopaedic implants that have been implanted in patients. A marker ID field is provided which stores the unique identifier of the marker attached to the orthopaedic implant. An implant data field of fields are provided for storing data items relating to the implant, such as the position of the marker relative to a feature of the implant, e.g. the centre of rotation for a hip implant or the surface for a knee implant. An implant graphics field is also provided for storing data items identifying graphics files which can be rendered to provide a three dimensional visual representation of the implant.

A patient scan table 378 stores data items relating to patient scans, such as CT, X-ray or fluoro scans. A patient ID field stores the unique patient identifier. A scan ID field stores a data item uniquely identifying each different scan carried out on the patient. A scan data field or fields store data items relating to the scan, such as the date of the scan and any position information or registration information relating to the position of the scan relative to the reference frame of the tracking system. A scan graphics field stores data items identifying the location of or the actual graphics files themselves from which a 3D representation of the patient's body part can be reconstructed.

Figure 7:
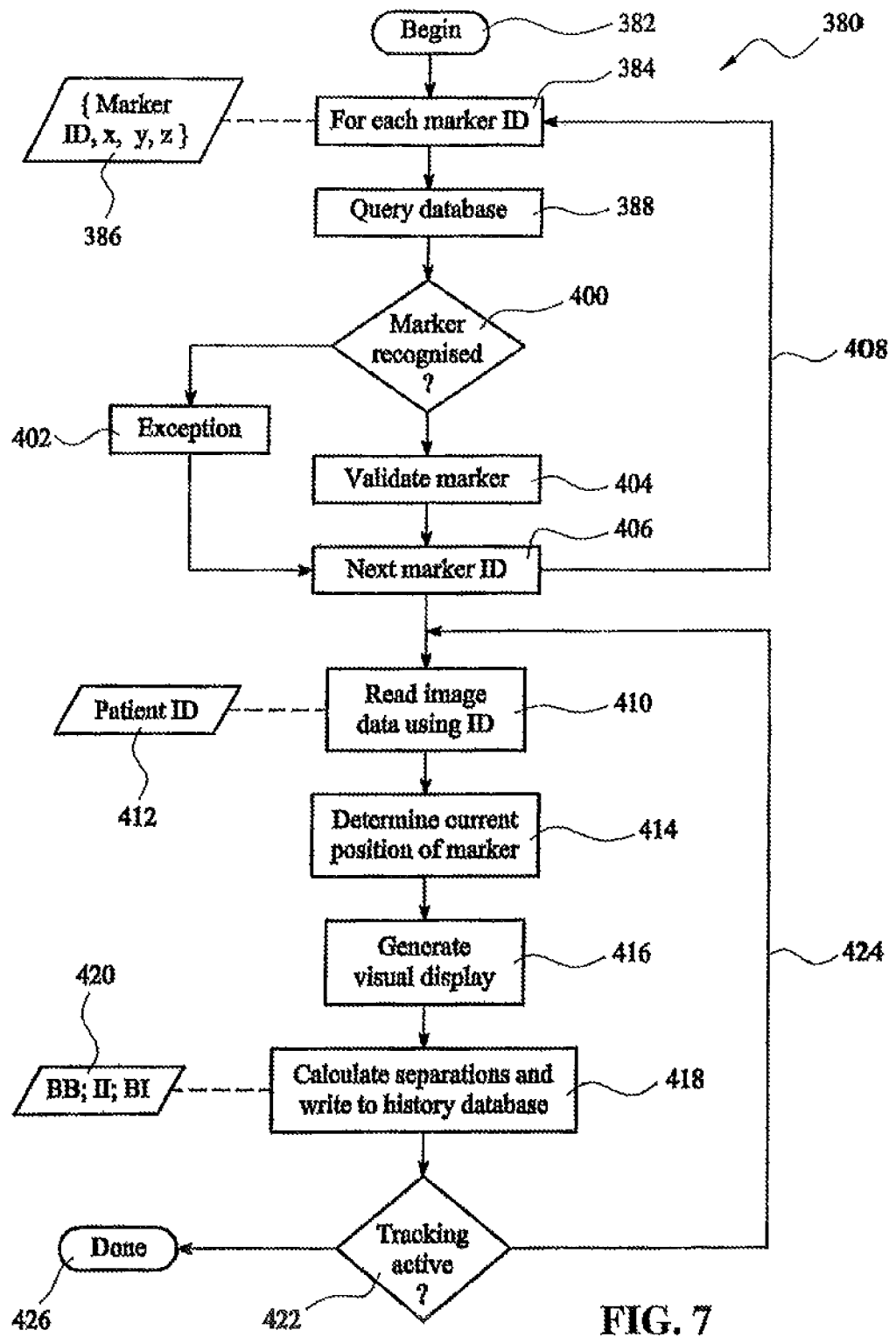
FIG. 7 shows a flow chart illustrating data processing operations of a data acquisition program part of the software architecture according to the invention.

With reference to FIG. 7 there is shown a flowchart showing various processes carried out by a computer program 380 implementing the data acquisition module 354. The program is called and initiates at step 382, in response to the entry of a command at the monitoring station by a user thereof to indicate that positional data is to be captured. Data can be captured with the patient static or with a dynamic patient, the latter allowing assessment of the kinematic performance of the patient to be carried out. The tracking system transmits RF power which is received by the implanted markers within the working volume and the markers power up and each marker transmits their marker ID and the six data items defining the marker's position and orientation within the reference to every tracking system. The tracking and data processing module 352 processes the received signals and passes a set of marker ID, position and orientation data items 286 for each of the markers to the data acquisition module.

At step 384, the data acquisition module receives the marker ID data item and at step 388 marker database 358 is queried to determine whether the received marker ID corresponds to a marker ID which has already been registered with the computer control system. If it is determined at step 400 that the received marker ID is not recognised, then at step 402 an exception handling procedure can be carried out, to allow a user to either register the marker ID, if a valid marker ID or to otherwise handle the non-recognised marker ID. If it is determined at step 400 that the marker has been recognised by the data acquisition module then the marker is flagged or otherwise identified as a valid marker whose position data is to be captured at step 404.

For example the patient may have several markers, all of which are valid markers for the patient but the user may indicate that data from only a subset of the markers, e.g. those corresponding to a knee joint, are to be captured during the current monitoring and assessment session. Validation of the marker can also include checking that the patient ID associated with the marker, corresponds to a patient ID entered into the data acquisition module by a user of the system. Then at step 406, process flow, as indicated by line 408, and the marker ID for the next marker is processed in the same way. Processing continues to loop in this manner until the marker IDs for all of the markers in the working volume have been interrogated and as a result of which the data acquisition module has validated and marked for capture positional data only from those markers of interest.

Sets of marker ID, position and orientation data 386 for each of the markers is continually supplied to the data acquisition module from the tracking data processing module 352 while the data acquisition program 380 is active. Program 380 as well as storing marker position data also provides a real time display of the marked bones and implants of the patient. At step 410, the program retrieves the patient ID data item 412 from the marker database 358. The patient ID should be the same for each of the marker IDs associated with the patient and so a one of the marker IDs can be used to carry out this step. At step 410, the program uses the patient ID to obtain scan image data and graphics data from database 362 and marker IDs to obtain implant data and implant graphics data associated with the implant bearing the marker from database 360.

Then at step 414, the current position within the reference frame of the tracking system for each of the markers and the orientation of each of the markers is determined. The "raw" positional data and orientation data is then stored, indexed by the marker ID for each of the markers in the patient's history database 356. Then at step 416, using the position and orientation of each of the markers, three dimensional graphical representations of the bones and implants are generated and displayed on the display screen of the computer control system 122. The patient's scan database includes scan data indicating the position of the marker in the scan image data and the scan graphics data is processed to render a 3D visual representation of the bone at the same orientation as the detected orientation of the marker. Similarly, for the orthopaedic implants, the implant data indicates the relative position of the marker in the implant and the implant graphics data is processed to render a three dimensional graphical representation of the implant in the orientation indicated by the marker orientation. The three dimensional bone images and three dimensional implant images generated in this way are displayed at step 416.

Then at step 418, the separation of a number of the markers is calculated and these separations can provide a representation of the orthopaedic performance of the patient. The separation between markers in the bones (the bone-bone separation) is calculated and stored in patient history database 356. The separation of the markers in the implants (the implant-implant separation) is calculated and stored in the patient history database. Also, the bone marker and implant marker separations, for all combinations of bone markers and implant markers (the bone-implant separation) are calculated and also stored in the patient history database 356.

If a static monitoring is being carried out, then once the positional data has been captured for the patient in the static position, then the tracking of the markers can cease. Alternatively, multiple positional data items can be captured and representations calculated and stored, so as to provide an averaged value derivable from the data stored in the patient history database. If the dynamic behaviour of the patient is being monitored, then multiple positional data items are captured and stored as the patient carries out the dynamic operations. At step 422, it is determined whether the tracking activity is still active and if so the process flow returns, as indicated by line 424 and at step 414, the current position of the markers is determined and the visual display is updated at step 416 and further positional data and other patient history data is calculated and stored in the patient history database at step 418. Data capture and storing proceeds in this way until it is determined at step 422 that tracking has ceased by which time the program ends at step 426.

A tracking event identifying data item can either be entered by a user of the system, or generated by the system and is stored in the patient's history database 356 so as to uniquely identify the captured patient data for the particular tracking event that has just been captured. Further tracking events can happen for the same patient, for example in a first tracking event, the static performance of the patient can be captured and in a second tracking event, the dynamic performance of the patient can be monitored, e.g. by having the patient walk passed the monitoring station or move from a sitting to a standing position or vice versa. Other static and dynamic operations can be carried out by the patient, such as moving a knee joint from a fully extended position and similarly moving a hip joint between its two extremes of motion.

When capturing data, the patient may be requested to remove all metal objects, such as belts, change, keys, jewelry, etc, as these can distort the magnetic field and reduce the accuracy of the system. The patient may also be required to remove their shoes to ensure that a consistent position is maintained for each visit. The following table provides a summary of an example of the different tracking events that can be captured for patients.

|  | Knee | Hip |
| --- | --- | --- |
| Static Tests | Sitting<br>Standing<br>Flexed Leg | Standing |
| Static Measurements | Bone-to-Bone (BB)<br>Bone-to-Implant (BI)<br>Implant-to-Implant (II) | Bone-to-Implant (BI)<br>Implant-to-Implant (II) |
| Dynamic Tests | Sitting to Standing | Walking |
| Dynamic Measurements | Bone-to-Bone (BB) | Bone-to-Bone (BB)<br>Bone-to-Implant (BI)<br>Implant-to-Implant (II) |
| Bone marker locations | 15 cm below knee joint on tibia<br>15 cm below knee joint on femur | Anterior iliac crest of pelvis<br>Epicondyle of femur (ouside of knee). |

For example, in knee monitoring, three static tests can be conducted, in three positions of the knee: sitting; standing; and with the leg lifted in a flexed position. While the patient is stationary, the system can take accurate readings to evaluate the status of the joint, for example to identify any potential loosening of the implant. Dynamic testing accuracy is influenced by the speed at which the markers are moving and therefore the support can be used to steady the patient to allow them to more slowly move from a sitting to a standing position, and vice versa.

In hip monitoring, an appropriate static test for the hip joint is the patient standing, as this loads the joint in the normal condition. A preferred dynamic loading test for the hip joint is walking. A treadmill may be provided at the monitoring station allowing the patient to remain still relative to the monitoring station while walking. Alternatively, a patient may take a step forward and then a step backward. Support hand rails may be beneficial to help patients maintain their balance.

The field generating coils can be provided on the floor of the tracking station or to the side of the tracking station. Depending on the size of the patient, the position of the coils relative to the patient may be adjusted to help ensure that the markers are located in the part of the magnetic field distribution allowing accurate measurements. The positions of the coils can also be adjusted so as to increase the amount of time that markers are located in the magnetic field distribution during dynamic tests to help increase the amount of data that can be captured (e.g. the amount of the gait cycle) and/or the accuracy of that data.

After the orthopaedic performance of the patient has been monitored, the captured data can then be used to assess the orthopaedic performance of the patient, either with the patient still on attendance or subsequently. Assessing the orthopaedic performance with the patient still present can be advantageous as the result of the assessment may indicate certain other tracking events which should be captured so as to improve the overall assessment of the orthopaedic performance of the patient.

A number of preoperative factors can affect the outcome of an orthopaedic procedure, such as total knee replacement (TKR) or arthroplasty (TKA). These factors can be of use in both pre and post operatively assessing the orthopaedic performance of a patient. For example, in TKA, factors relating to the knee function can be useful, such as PROM/AROM, instability (AP, IE and/or VV), weight bearing tests and gait. Factors relating to leg alignment can be useful, such as the leg mechanical axis (including differences between supine and weight bearing), coronal alignment, the femoral axis or line, the tibial axis or line, the patella, the joint line and the articular contact. Factors relating to the patient's state can be useful, such as the body mass index, sex, population, origin, bone osteophytes and proprioception. Factors relating to the patients feelings can be useful, such as pain, the patient's level of activity and life expectancy. Any one or any combination of these factors can be of use in the pre and post operative orthopaedic assessment of the patient.

Figure 8:
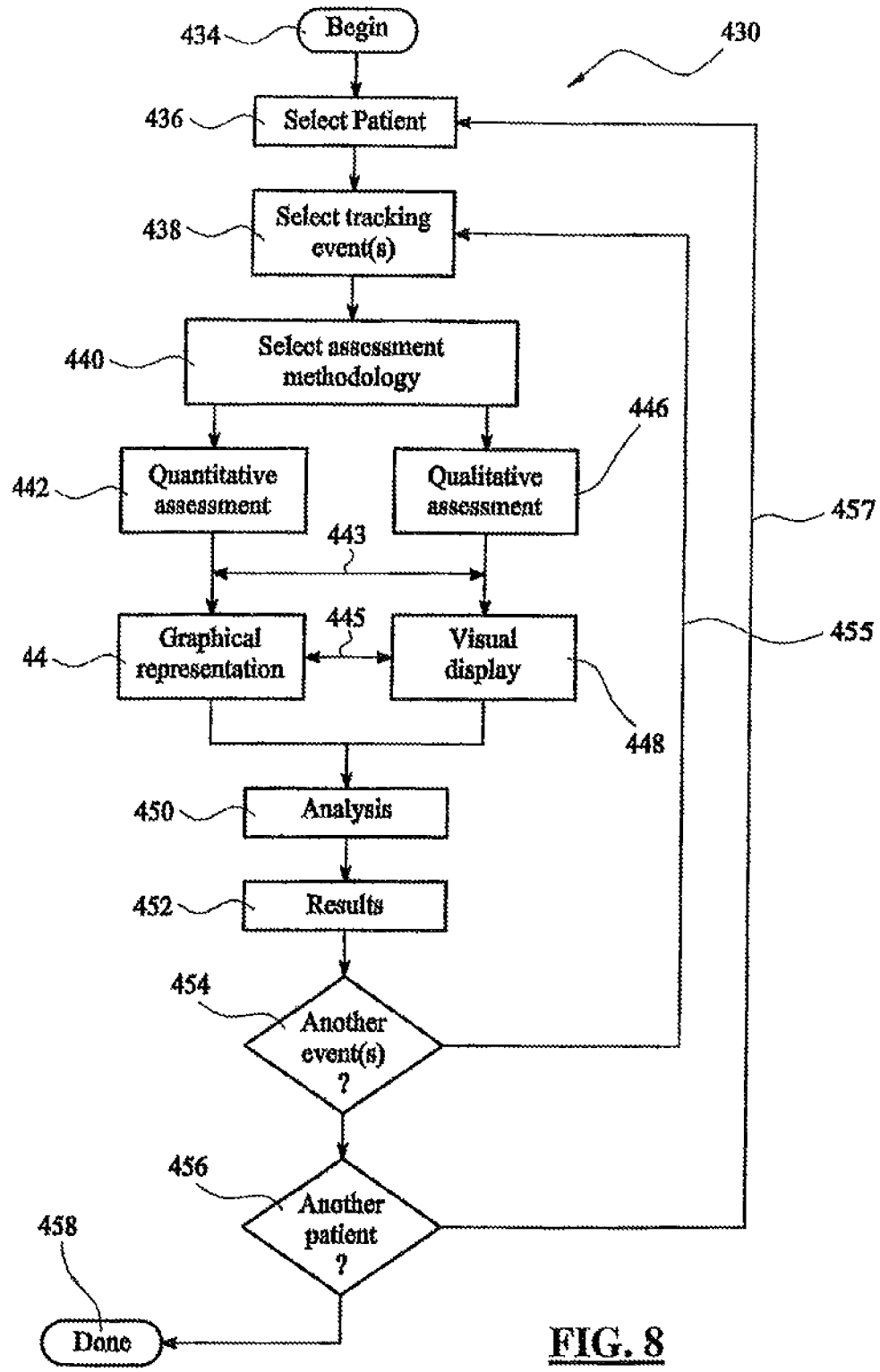
FIG. 8 shows a flow chart illustrating data processing operations of an assessment program part of the software architecture according to the invention.

The assessment of the orthopaedic performance of the patient is carried out using a further software module 364. FIG. 8 show a flowchart illustrating various processes carried out by computer system 122 by a computer program 430 implementing the assessment module 364.

The assessment module primarily uses the captured patient data history data for the patient, and for other patients, in order to provide an assessment of the orthopaedic performance of the patient. The assessment module can also access the marker, implant and patient scan databases, particularly in instances where a graphical representation of the performance of the patient is to be displayed.

Figure 9:
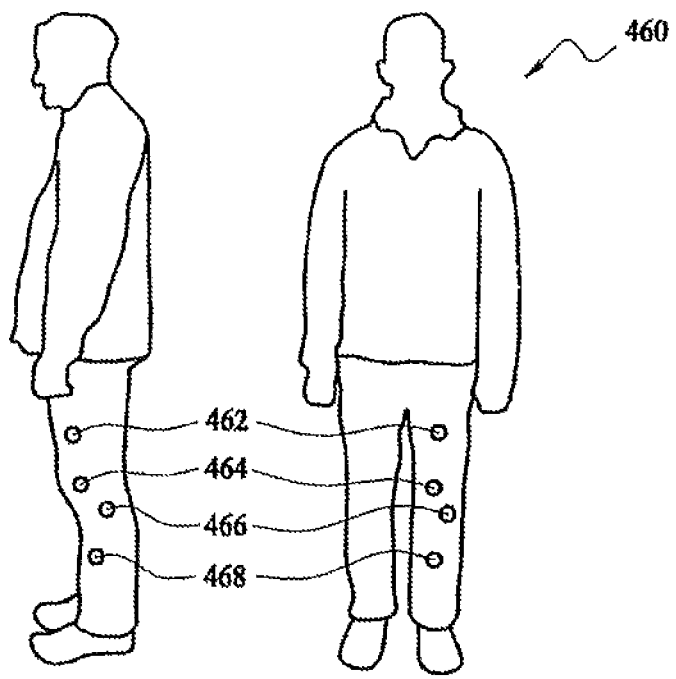
FIG. 9 shows a patient with a number of implanted markers who is going to have their orthopaedic performance monitored and assessed.

With reference to FIG. 9, there is shown a side and front view of a patient 460 who has had a total knee replacement operation. The patient has a femoral implanted marker 462, a femoral implant marker 464, a tibial implant marker 466 and a tibial implanted marker 468. The assessment of the orthopaedic performance of patient 460 will be described in greater detail below with regard to the orthopaedic performance of the patient's knee although it will be appreciated that other orthopaedic performances can be assessed using other combinations of bone markers and/or orthopaedic implant markers.

A user of the computer system 122 uses to assessment module 364 to carry out an orthopaedic assessment of the patient 460 and at step 434, program 430 is called and initiates. At step 436, the user enters the patient ID for the patient so as to select the patient history by using the assessment of the patient. At step 438, the user enters a tracking event identifier thereby selecting which tracking event data set or sets of data sets to use in the assessment of the patient. A variety of different assessment procedures or methodologies can be used depending on the nature of the orthopaedic performance to be assessed. The user of the system will typically be a medical professional and can use their medical training and experience to decide which assessment methodology or methodologies are appropriate depending on the performance being assessed. The user is presented with various assessment methodologies and at step 440, the user selects which methodology to use.

In general, assessment methodologies can be generally categorised as being qualitative or quantitative. In general, a qualitative assessment methodology considers the overall behaviour of the orthopaedic performance of the patient and can include a value based judgement assessment of the performance of the patient. A quantitative assessment methodology generally includes determining some metric or other quantitative measure of the orthopaedic performance of the patient and using the orthopaedic metric as part of the assessment of the performance. It will be appreciated that some assessment methodologies can include both qualitative and quantitative aspects, such as pattern recognition processes which compare the overall orthopaedic performance of the patient with other data sets but while also using quantitative measures of or derived from the data sets.

If a quantitative assessment methodology is selected, then at step 442, a quantitative assessment process is carried out which can include providing a graphical representation with the orthopaedic performance of the patient at step 444 and/or a visual display of the patient's actual orthopaedic performance at step 448.

Figure 10:
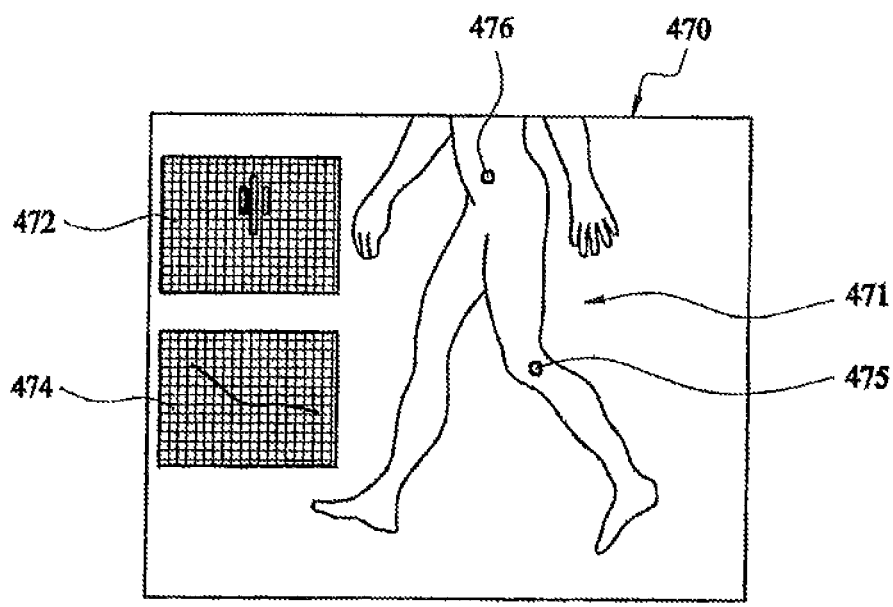
FIG. 10 shows an example of a screen shot illustrating a combined qualitative and quantitative orthopaedic assessment.

With reference to FIG. 10, there is shown a screen shot 470 illustrating the display of a first graphical representation 472 and a second graphical representation 474 of the orthopaedic performance of the patient. Also shown is a visual display 471 of the performance of the patient, which can include an animated display of the patient's orthopaedic performance, displaying both their body parts and markers, e.g. markers 476 and 475. The animated display can be reconstructed from the patient history data and the implant and patient scan data from databases 360 and 362 respectively. In the illustrated example, a kinematic event, that is the patient walking is being assessed. Graphical representation 472, shows the change in position of a one of the markers as the patient walks and is reconstructed from the "raw" marker position data from the patient history database. Graphical representation 474, displays the variation in the bone-bone separation as the patient walks. The bone-bone separation provides a representation of the orthopaedic performance which can be used to assess the general kinematic behaviour of the patient's leg after the replacement of the patient's knee joint.

In other embodiments, graphical representation 474, can show the implant-implant separation which can be used to assess the degree of wear of the implant. If implants are wearing, then the separation of two fixed points on the implants would be expected to change over time and improper wearing of the implants can be detected from the implant-implant separation. The implant-implant separation can also be used to provide an assessment of the success of the implanted prosthetic knee joint as an improper functioning of the knee joint e.g. owing to incorrect positioning of either the implant components, can also be assessed from the behaviour of the implant-implant separation.

In another embodiment, graphical representation 474 can display the bone implant separation, e.g. the separation between the tibia and tibial implant or the separation between the femur and the femoral implant which indicates the degree of relative movement between the bone and implant which can indicate a loosening of the implant in the bone which may lead to failure of the implant. Based on an assessment of this graphical representation of the orthopaedic performance of the patient, it can be possible to predict the likelihood of implant failure if excessive implant movement is identified.

As represented by lines 443, a quantitative assessment can make use of either a graphical representation or a visual display of the patient's orthopaedic performance and as indicated by line 445, the user can toddle between a graphical representation or a visual display or, as illustrated in FIG. 10, display them at the same time.

Figure 12:
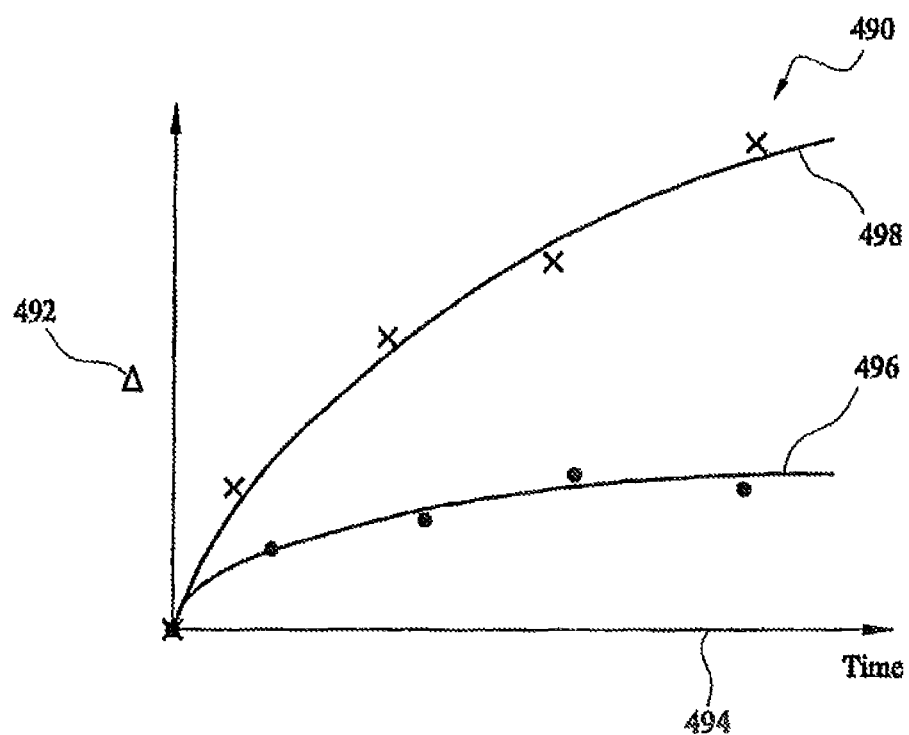
FIG. 12 shows a graphical representation of a static assessment of orthopaedic performance as a function of implantation time.

With reference to FIG. 12, there is shown a graphical representation 490 of the orthopaedic performance of the patient 460. Graphical representation 490 shows a graph of bone implant separation 492 as a function of time, where the time axis covers several monitoring events over a period of time e.g. several weeks, months or years. By way of example only, bone implant separation 492 can be the femoral bone implant separation. An initial bone-implant separation can be taken as a base line separation which is subtracted from subsequent measurements so as to more clearly illustrate variations from the base line. In alternate embodiments, the actual bone implant separation values can be used. Line 496 represents a curve fitted to five bone implant separations for the patient in a particular position, e.g. standing.

A qualitative assessment of this graphical representation would be that the overall form of line 496 indicates that the bone implant separation has settled to a fairly constant value and therefore further loosening of the implant in the bone is unlikely and the implant can be considered unlikely to fail. The assessment that the implant is unlikely to fail can be made by a skilled user of the system or the system itself can carry out the assessment at analysis step 450, for example by calculating the gradient of the graph at several points along the graph and calculating the measured gradient with gradients obtained from other patients whose implants have not failed. Therefore historical data collected from other patients is used as the basis of the comparison. It will therefore be appreciated that in this latter aspect, a quantitative approach is also used in assessing the performance of the patient. Then at step 452, the result of that quantitative assessment can be displayed to the user, e.g. by categorising the implant as being unlikely to fail or not being likely to fail.

Line 498 shows a fit to a second set of five bone implants separation data points. A skilled user may carry out a qualitative assessment of this representation of the orthopaedic performance of the patient and determine at analysis step 450 that as the bone implant separation is still increasing there is a significant likelihood of implant failure and therefore that remedial action is required for the patient. A quantitative assessment could involve calculating local gradients or the overall gradient of line 498 and comparing those gradients with threshold values derived from other patient histories. For example, a change in bone implant separation of approximately 0.2 mm per year can be indicative of implant failure and therefore if the local gradient or overall gradient of line 498 exceeds that cut off value, then at step 452, the patient's orthopaedic performance can be categorised as implant failure and the patient can be referred for remedial intervention. A further qualitative approach to assessing the orthopaedic performance of the patient using graphical representation 490 will now be described. Line 498 represents the orthopaedic performance of the patient under assessment. Line 496 represents the performance of another patient or the average performance of a group of patients whose implants have not failed. By comparing the features of line 498 with 496, a qualitative assessment of the orthopaedic performance can be obtained. In a more quantitative approach, a pattern matching algorithm can be used to obtain a quantitative indication of the similarity between lines 498 and 496 and that goodness of fit metric derived from this analysis can be used at step 452 to generate the results of the assessment.

Although the separation 492 using FIG. 12 has been described as the bone-bone separation, it will be appreciated that the bone-implant and also implant-implant separations can also be used and that other representations of the orthopaedic performance of the patient derived from the raw implant and bone position data can also be used in the assessment.

The above discussion also covers the qualitative assessment of the orthopaedic performance of the patient which can be selected at step 446 and carried out using graphic representation 490 at step 444. Alternatively, the qualitative assessment 446 can be carried out using the visual display 471 of the patient's orthopaedic performance. For example, a skilled user can observe an animated visual display of the patient and based on their skill or experience, carry out an analysis of that visual display which can result in a categorisation of the performance, e.g. that the orthopaedic performance is currently acceptable or is currently unacceptable, or may be likely to deteriorate or fail in future.

Figure 11:
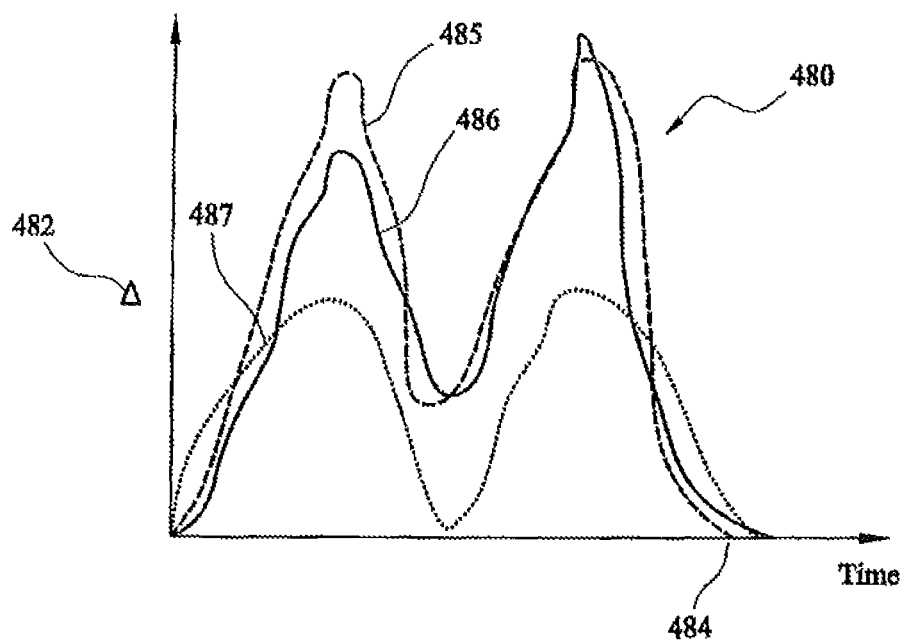
FIG. 11 shows a graphical representation of a kinematic assessment of orthopaedic performance.

With reference to FIG. 11, there is shown a further graphical representation of the orthopaedic performance of the patient which can be used in a qualitative or quantitative assessment. Graphical representation 480 illustrates a graph of the bone-bone or bone-implant separation for a two of a function of time during a kinematic patient event. In the illustrated representation, graphical representation 480 shows the variation in separation during a single walking cycle of the patient and so can be used as part of a gait analysis.

In a first, qualitative approach, line 485 represents a collection of separations calculated from the bon-bone positions as a function of time as the patient walks passed the monitoring station. Line 486 corresponds to line 485 which is derived from a previous tracking event, e.g. six months previously. Under a qualitative assessment, a user of the system may determine that the representations of the orthopaedic performance 485, 486 are sufficiently similar that no significant changes, e.g. in the implant wear have occurred. Line 487 illustrates the same data captured for a tracking event after the tracking event from which lines 485 and 486 were derived. From a qualitative assessment, it may be considered that the change between the orthopaedic performance represented by line 487 and representations 485, 486 of the previous orthopaedic performance are sufficient that the result of this analysis is that the implants are improperly wearing and that remedial intervention would be advisable.

In a more quantitative approach, at analysis step 450, the computer program can determine the heights of each of the peaks in the gait analysis plots and if the difference in the heights between subsequent gait analysis plots are sufficiently different, e.g. as assessed by comparison with a threshold or cut off value, a result can automatically be generated. The result may be categorisation of the implant as failing owing to improper wear. Alternatively, if separation 482 is a bone-bone separation, then the result may be that the implant is considered to be improperly positioned such that the patient's kinematic performance has not been improved or has worsened as a result of the implanted knee joint. For example, plot 485 or 486 may correspond to the patient's orthopaedic performance prior to implantation of the replacement knee. Therefore result process 452 can provide an indication of the success with which the knee replacement procedure was carried out.

In alternate embodiments, rather than comparing the patient's orthopaedic performance with their own prior orthopaedic performance, the patient's orthopaedic performance can be compared with a model orthopaedic performance or with the orthopaedic performance of another patient or other patients. For example, line 485 may represent the theoretical behaviour of an implant-implant or bone-bone separation, for perfectly positioned orthopaedic implants. Therefore at step 450, the analysis can be of a comparison of the representation of the patient's orthopaedic performance with a theoretical or model performance. In one embodiment, the goodness or fit of the representation of the patient's performance to the model performance can be obtained and the goodness of fit can be used as an orthopaedic performance assessment metric. The assessment metric can then be used by results process 452 by comparison with a threshold or cut off value in order to classify the patient's orthopaedic performance. For example if the goodness of fit is sufficiently low, the patient can be categorised as requiring corrective surgery or other action or treatment so as to ameliorate the problem.

In another embodiment, line 485 may represent the orthopaedic performance of a different patient having had a similar operation carried out and again the goodness of fit of the patient's orthopaedic performance with the other patient's orthopaedic performance can be determined in an analysis step 450 and used in results step 452. In a further embodiment, line 485 can represent an average over a number of patients having had the same surgical procedure carried out and which has been determined to be a success. Alternatively, the representation of the patient's orthopaedic performance 486 can be compared with a representation of an orthopaedic performance which can be considered to be unsuccessful, e.g. line 487. For example a certain lower threshold model performance 487 can be determined and the patient's orthopaedic performance can be determined to be a success if it is considered to be sufficiently dissimilar to the unsuccessful performance represented by line 487. As well as being a model or theoretical performance, line 487 could also be the monitored orthopaedic performance of a patient having had an unsuccessful operation or an average of a group of patients having had unsuccessful operations.

Irrespective of whether the comparison is with a representation of a successful operation or a representation of an unsuccessful operation, a quantitative assessment includes obtaining some quantitative measure of the similarity between the patient's performance and some other performance and using that metric to categorise the patient's performance so as to provide a result at step 452. One particularly suitable method for analysing and categorising the patient's orthopaedic performance would be to use a pattern recognition technique, such as one implemented by a neural network. Representations of successful and unsuccessful surgical procedures can be used as the trading set for the network and then the current's patient orthopaedic performance can be submitted to the neural network for analysis with the neural network determining whether the representation of the patient's performance corresponds to a successful or unsuccessful treatment. The determination of the network can then be used to generate the results which are output at step 452.

A pattern recognition approach can also be used for comparing the orthopaedic performance of the patient over multiple monitoring events, several months or years apart, with a model or other patient behaviours as discussed previously with reference to FIG. 12. The pattern matching approach can be used for bone-bone, bone-implant and also implant-implant separations. The assessment method is not limited to only patients having orthopaedic implants. As indicated above, separation 482 can be a bone-bone separation in which case the effect of an orthopaedic surgical procedure, e.g. a cruciate ligament replacement operation, can be assessed using the present invention.

As discussed above with reference to FIGS. 11 and 12, a user can instruct the computer to carry out an analysis of the representations of the orthopaedic performance of the patient at step 450. Following the analysis, at step 452, the results of the analysis can be determined and displayed to the user. The results of the analysis can include generating a categorisation of the orthopaedic performance of the patient. For example the orthopaedic performance of the patient could be categorised as acceptable, in which case no intervention would be required, unacceptable, in which case intervention may be required. The degree to which the performance is considered to be acceptable can further be used in order to generate an indication of the time frame after which a next monitoring of the patient's performance and assessment should be carried out.

Statistical tests can be applied both to the representations of the orthopaedic performance of the patient and to the quantitative results of the analysis. Statistical tests can generally be used to give an indication of the reliability of the assignment of a value to a one of two groups of values. For example a confidence that an effect is real as opposed to coincidental or not having any statistical significance can be obtained. In general a statistical test can be used to determine the confidence that the patient can be categorised in any of the categories, or that the representation or a metric, can be assigned to an acceptable performance or an unacceptable performance. For example a group of metrics for patients whose implants have been found to be successful and a group of metrics for patients whose implants have been found to be unsuccessful can be obtained form the patient history. Then for a current patient, the confidence that the patient's metric can be considered to fall in one of the two groups can be assessed using the statistical test. Suitable statistical tests would include a Chi-squared test, a Z-test and a rank sum test and other similar tests.

For example if the patient's performance is determined to be close to acceptable, then the program may determine a time before a next assessment which is proportional to the extent to which the performance is found to be acceptable. For example if the performance was determined to be close to being unacceptable then a short period of time may be set for the next assessment, e.g. one week or one month. Alternatively, if the performance is determined to be acceptable by a significant amount, then a next assessment may be scheduled for several months, e.g. six months from the current assessment.

Based on an implant-implant separation assessment, the orthopaedic performance may be categorised as indicating acceptable or unacceptable wear of the implants. If the performance is categorised as unacceptable wear, then the patient may be categorised as requiring intervention in order to ameliorate the problem. Based on an assessment of bone-implant separation, the patient may be categorised as likely to experience implant failure and some measure of the likelihood of implant failure can be generated by the computer program 430 and either displayed to the user or used in the categorisation of the likelihood of implant failure. For example degrees of implant failure likelihood can be displayed in the results process 452. Again, the time before a next assessment of the patient can also be based on the likelihood of implant failure, with a shorter period before a next assessment assigned to a patient with a high likelihood of implant failure.

After the results have been generated at step 452, at step 454, the user can enter a command to select a further tracking event to assess. For example the first tracking event may have been a static tracking event and the further tracking event may be a dynamic tracking event. Process flow returns at line 454 and processing proceeds as described above in relation to the patient history for the newly selected tracking event. Although not indicated in FIG. 8, after analysis of any other tracking events has been completed, in one embodiment, the results of the assessments of different types of tracking events are combined to provide an overall assessment of the patient's orthopaedic performance. For example kinematic, static, loaded and unloaded events may in combination provide a better indication of the overall likelihood of failure of the orthopaedic performance of the patient.

After the orthopaedic performance of the patient has been completed, at step 456 the user can enter a command to select a further patient for assessment and process flow returns as indicated by line 457 and at step 436, the user selects the new patient to assess. After it has been determined that all patients have been assessed, then at step 458 the assessment method ends.

Generally, embodiments of the present invention employ various processes involving data stored in or transferred through one or more computer systems. Embodiments of the present invention also relate to an apparatus for performing these operations. This apparatus may be specially constructed for the required purposes, or it may be a general-purpose computer selectively activated or reconfigured by a computer program and/or data structure stored in the computer. The processes presented herein are not inherently related to any particular computer or other apparatus. In particular, various general-purpose machines may be used with programs written in accordance with the teachings herein, or it may be more convenient to construct a more specialized apparatus to perform the required method steps. A particular structure for a variety of these machines will appear from the description given below.

In addition, embodiments of the present invention relate to computer readable media or computer program products that include program instructions and/or data (including data structures) for performing various computer-implemented operations. Examples of computer-readable media include, but are not limited to, magnetic media such as hard disks, floppy disks, and magnetic tape; optical media such as CD-ROM disks; magneto-optical media; semiconductor memory devices, and hardware devices that are specially configured to store and perform program instructions, such as read-only memory devices (ROM) and random access memory (RAM). The data and program instructions of this invention may also be embodied on a carrier wave or other transport medium. Examples of program instructions include both machine code, such as produced by a compiler, and files containing higher level code that may be executed by the computer using an interpreter.

Figure 13:
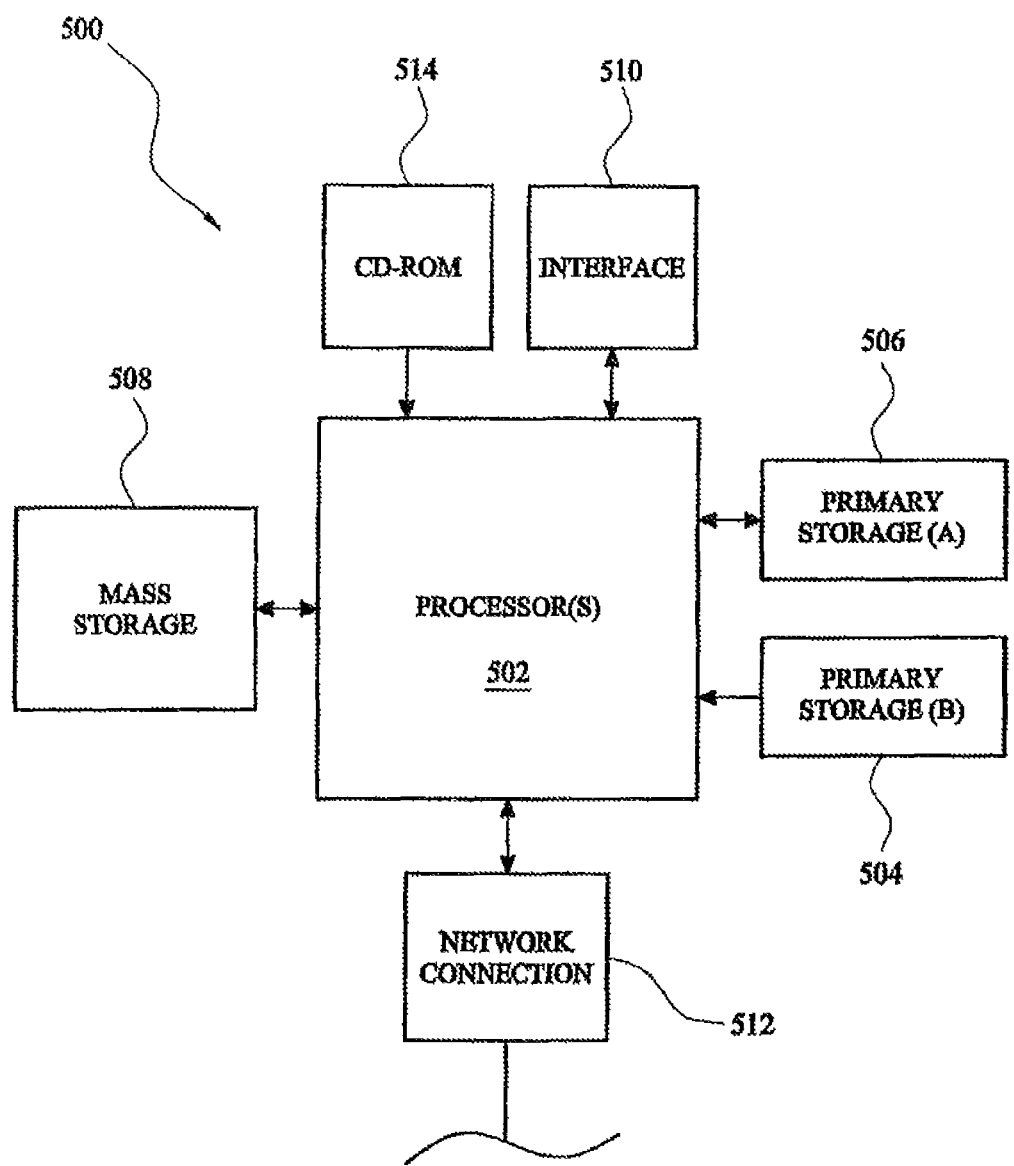
FIG. 13 shows a schematic block diagram of a computer part of the orthopaedic monitoring system shown in FIG. 2.

FIG. 13 illustrates a typical computer system that, when appropriately configured or designed, can serve as an image analysis apparatus of this invention. The computer system 500 includes any number of processors 502 (also referred to as central processing units, or CPUs) that are coupled to storage devices including primary storage 506 (typically a random access memory, or RAM), primary storage 504 (typically a read only memory, or ROM). CPU 502 may be of various types including microcontrollers and microprocessors such as programmable devices (e.g., CPLDs and FPGAs) and unprogrammable devices such as gate array ASICs or general purpose microprocessors. As is well known in the art, primary storage 504 acts to transfer data and instructions uni-directionally to the CPU and primary storage 506 is used typically to transfer data and instructions in a bi-directional manner. Both of these primary storage devices may include any suitable computer-readable media such as those described above. A mass storage device 508 is also coupled bi-directionally to CPU 502 and provides additional data storage capacity and may include any of the computer-readable media described above. Mass storage device 508 may be used to store programs, data and the like and is typically a secondary storage medium such as a hard disk. It will be appreciated that the information retained within the mass storage device 508, may, in appropriate cases, be incorporated in standard fashion as part of primary storage 506 as virtual memory. A specific mass storage device such as a CD-ROM 514 may also pass data uni-directionally to the CPU.

CPU 502 is also coupled to an interface 510 that connects to one or more input/output devices such as such as video monitors, track balls, mice, keyboards, microphones, touch-sensitive displays, transducer card readers, magnetic or paper tape readers, tablets, styluses, voice or handwriting recognizers, or other well-known input devices such as, of course, other computers. Finally, CPU 502 optionally may be coupled to an external device such as a database or a computer or telecommunications network using an external connection as shown generally at 512. With such a connection, it is contemplated that the CPU might receive information from the network, or might output information to the network in the course of performing the method steps described herein.

Although the above has generally described the present invention according to specific processes and apparatus, the present invention has a much broader range of applicability. In particular, aspects of the present invention is not limited to any particular kind of orthopaedic performance and can be applied to virtually any joint or body structure, whether including an implant or implants or not, with relatively moving bones where an understanding of the performance of the joint or body structure is desired. Thus, in some embodiments, the techniques of the present invention could provide information about the success of surgery not involving implants, e.g. a cruciate ligament operation, as well as implant related surgical techniques. One of ordinary skill in the art would recognize other variants, modifications and alternatives in light of the foregoing discussion.

It will also be appreciated that the invention is not limited to the specific combinations of structural features, data processing operations, data structures or sequences of method steps described and that, unless the context requires otherwise, the foregoing can be altered, varied and modified. For example different combinations of structural features can be used and features described with reference to one embodiment can be combined with other features described with reference to other embodiments. Similarly the sequence of the methods step can be altered and various actions can be combined into a single method step and some methods steps can be carried out as a plurality of individual steps. Also some of the structures are schematically illustrated separately, or as comprising particular combinations of features, for the sake of clarity of explanation only and various of the structures can be combined or integrated together or different features assigned to other structures.

What is claimed is:

1. A medical system, comprising:
    a bone anchor configured to be implanted in a bone of a patient during a surgical procedure, the bone anchor having a bone-engaging surface feature; and
    a processor configured to
        determine at least one of a position and an orientation of the bone anchor within the bone,
        assess an orthopaedic performance of the patient based on the determined at least one of position and orientation of the bone anchor,
        use the determined at least one of position and orientation to calculate a representation of the orthopaedic performance, and
        compare, using a neural network, the representation with a predetermined model representation of orthopaedic performance.

2. The system of claim 1, wherein the processor being configured to assess the orthopaedic performance of the patient includes the processor being configured to determine whether the orthopaedic performance of the patient is successful or unsuccessful based on the comparing.

3. The system of claim 1, wherein the processor is configured to update the neural network to reflect the orthopaedic performance of the patient to allow the orthopaedic performance of the patient to be considered in assessments of orthopaedic performances of other patients.

4. The system of claim 1, wherein the representation includes at least one of a visual representation, graphical representation, and animated representation of the determined at least one of position and orientation for display on a display screen.

5. The system of claim 1, wherein the processor being configured to assess the orthopaedic performance of the patient includes the processor being configured to use the determined at least one of position and orientation to calculate a metric representative of the orthopaedic performance and to categorize the orthopaedic performance based on the metric.

6. The system of claim 5, wherein the processor being configured to categorize includes the processor being configured to categorize the orthopaedic performance into a category selected from the group consisting of the patient requiring further periodic orthopaedic assessment, the patient not requiring further orthopaedic assessment, the patient requiring surgical intervention, the patient not requiring surgical intervention, the patient being likely to experience failure of the bone anchor, and the patient not being likely to experience failure of the bone anchor.

7. The system of claim 1, further comprising an electronic monitoring system configured to transmit an electronic signal, wherein the processor is configured to receive the electronic signal and is configured to determine the at least one of position and orientation of the bone anchor based on the received electronic signal.

8. The system of claim 7, wherein the signal includes a plurality of signals each representative of information gathered at separate points in time;
the processor being configured to determine the at least one of position and orientation of the bone anchor includes the processor being configured to determine the at least one of position and orientation of the bone anchor corresponding to each of the points in time based on the signal associated with the point in time; and
the processor being configured to assess the orthopaedic performance of the patient includes the processor being configured to compare the determined at least one of position and orientation corresponding to each of the points in time.

9. The system of claim 8, wherein adjacent ones of the separate points in time are separated from one another by an amount of time in a range of one week to ten years.

10. The system of claim 7, wherein the electronic monitoring system includes at least one sensor, and the signal is based on information sensed by the at least one sensor.

11. The system of claim 10, wherein the at least one sensor and the bone anchor are independent elements.

12. The system of claim 1, further comprising an insertion instrument configured to removably couple to the bone anchor and to insert the bone anchor into the bone.

13. The system of claim 1, wherein the surface feature is selected from the group consisting of a thread, a barb, and a rib.

14. The system of claim 1, wherein the processor is configured to receive and analyze a signal from a single sensor and is configured to determine the at least one of position and orientation of the bone anchor based on the signal from the single sensor.

15. The system of claim 1, wherein the processor is configured to receive and analyze a signal from each of a plurality of sensors and is configured to determine the at least one of position and orientation of the bone anchor based on the signals from the plurality of sensors.

16. The system of claim 1, further comprising a memory storing therein the predetermined model representation of orthopaedic performance and storing therein instructions that cause the processor to determine the at least one of the position and the orientation of the bone anchor within the bone, assess the orthopaedic performance of the patient based on the determined at least one of position and orientation of the bone anchor, use the determined at least one of position and orientation to calculate the representation of the orthopaedic performance, and compare, using the neural network, the representation with the predetermined model representation of orthopaedic performance.

17. The system of claim 16, wherein the processor and the memory are included in a computer system that is external to the patient.

18. The system of claim 1, wherein the predetermined model representation of orthopaedic performance is a theoretical orthopaedic performance.

19. The system of claim 1, further comprising a second bone anchor configured to be implanted in a bone of a second patient during a second surgical procedure, the second bone anchor having a bone-engaging surface feature;
wherein the processor is configured to
determine at least one of a position and an orientation of the second bone anchor within the bone of the second patient,
assess an orthopaedic performance of the second patient based on the determined at least one of position and orientation of the second bone anchor,
update the neural network to reflect the orthopaedic performance of the patient, and
compare, using the updated neural network, the orthopaedic performance of the patient with the orthopaedic performance of the second patient to assess whether the orthopaedic performance of the second patient is successful or unsuccessful.

20. A medical system, comprising:
a bone anchor configured to be implanted in a bone of a patient during a surgical procedure, the bone anchor having a bone-engaging surface feature; and
a processor configured to
determine an orientation of the bone anchor within the bone based on pitch, yaw, and roll orientations of the bone anchor, and
assess an orthopaedic performance of the patient based on the determined orientation of the bone anchor.

21. The system of claim 20, wherein the processor being configured to assess the orthopaedic performance of the patient includes the processor being configured to use the determined orientation to calculate a representation of the orthopaedic performance, and being configured to compare the representation with a predetermined model representation of orthopaedic performance.

22. The system of claim 21, wherein the processor being configured to compare the representation with a predetermined model representation of orthopaedic performance includes the processor being configured to use a neural network.

* * * * *